(12) United States Patent
Gorgoulis et al.

(10) Patent No.: US 10,947,390 B2
(45) Date of Patent: Mar. 16, 2021

(54) COMPOUNDS FOR THE DETECTION OF SENESCENT CELLS

(71) Applicant: THE UNIVERSITY OF MANCHESTER, Manchester (GB)

(72) Inventors: Vassilis Gorgoulis, Athens (GR); Paul Townsend, Manchester (GB); Panayiotis Marakos, Athens (GR); Nikolaos Lougiakis, Athens (GR); Nicole Pouli, Athens (GR); Nikolaos Kastrinakis, Athens (GR)

(73) Assignee: THE UNIVERSITY OF MANCHESTER, Manchester (GB)

( * ) Notice: Subject to any disclaimer, the term of this patent is extended or adjusted under 35 U.S.C. 154(b) by 58 days.

(21) Appl. No.: 16/313,617

(22) PCT Filed: Jun. 28, 2017

(86) PCT No.: PCT/GB2017/051889
§ 371 (c)(1),
(2) Date: Dec. 27, 2018

(87) PCT Pub. No.: WO2018/002614
PCT Pub. Date: Jan. 4, 2018

(65) Prior Publication Data
US 2019/0315966 A1    Oct. 17, 2019

(30) Foreign Application Priority Data
Jun. 28, 2016 (GB) .................................. 1611208.8

(51) Int. Cl.
*G01N 1/30* (2006.01)
*C09B 31/053* (2006.01)

(52) U.S. Cl.
CPC ............. *C09B 31/053* (2013.01); *G01N 1/30* (2013.01); *G01N 2001/302* (2013.01)

(58) Field of Classification Search
CPC combination set(s) only.
See application file for complete search history.

(56) References Cited

U.S. PATENT DOCUMENTS

| | | |
|---|---|---|
| 2015/0065620 A1 | 3/2015 | Banning et al. |
| 2015/0065697 A1 | 3/2015 | Banning et al. |

FOREIGN PATENT DOCUMENTS

| | | |
|---|---|---|
| EP | 0 460 504 A1 | 12/1991 |
| EP | 0 460 504 B1 | 4/1994 |
| EP | 1 462 485 A1 | 9/2004 |
| WO | 2014/111112 A1 | 7/2014 |
| WO | 2016/096085 A1 | 6/2016 |

OTHER PUBLICATIONS

Georgakopoulou, EA et al., Aging 2013 vol. 5 pp. 38-50.*
Georgakopoulou et al., "Specific lipofuscin staining as a novel biomarker to detect replicative and stress-induced senescence. A method applicable in cryo-preserved and archival tissues," *Aging* 5(1):37-50, 2013.
Great Britain Search Report, dated Mar. 30, 2017, for Great Britain Application No. 1611206.2, 3 pages.
Great Britain Search Report, dated Mar. 29, 2017, for Great Britain Application No. 1611208.8, 4 pages.
O'Brien et al., "N,N'—Disubstituted Naphthyl(Azo)-2,3-Dihydroperimidine Blue Dyes Exhibiting High Solubility in Ferroelectric Liquid Crystal Hosts," *Mol. Cryst. Liq. Cryst.*, 220:167-175, 1992.

* cited by examiner

*Primary Examiner* — Heidi Reese
(74) *Attorney, Agent, or Firm* — Seed IP Law Group LLP

(57) ABSTRACT

The present disclosure relates to de novo synthesized, chemical compounds of the formula (1) or (2) that function as senescent cell detectors wherein $R_1$, $R_2$, $R_3$, $R_4$ and Z are as defined herein. The present invention also relates to processes for the preparation of these compounds, to their use in the detection of senescent cells, to methods of detecting senescence in cells and to kits comprising said compounds. The compounds have the ability to react with lipofuscin, in an analogous manner to the histochemical dye Sudan Black B (SBB).

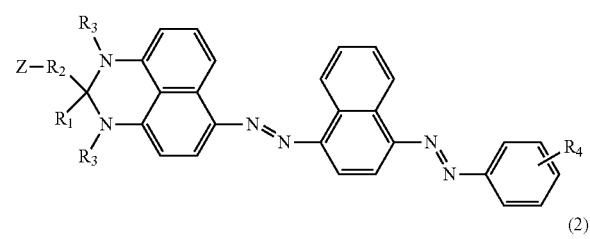

24 Claims, 3 Drawing Sheets a.

Thymus

Cortex | Medulla a. b.

COMPOUNDS FOR THE DETECTION OF SENESCENT CELLS

FIELD OF THE INVENTION

The present disclosure relates to novel chemical compounds that function as senescent cell detectors. The present invention also relates to processes for the preparation of these compounds, to their use in methods for the detection of senescent cells, and to kits comprising these compounds.

BACKGROUND

Senescence is a "cellular state" that reflects a stress condition encountered by a cell rather than a cell becoming "aged". It is characterized by non-reversible arrest of the cell cycle [Gorgoulis & Halazonetis, Curr Opin Cell Biol 2010] and modified cellular function. One of its forms can be induced in response to telomere attrition of chromosomal ends, after an extended number of cell divisions. This form of senescence is known as "replicative senescence". Cells can also enter another form of senescence, independently of telomere length, termed "premature senescence" in response to stressful pathophysiological stimuli [Dimri et al, Proc Natl Acad Sci USA 1995] such as, oncogenic stimuli, increased levels of free radicals (for example reactive oxygen species—ROS) and cell-cell fusion.

Senescence is currently believed to contribute to the processes of development, ageing, cancer (acting both as a tumor barrier and a promoter), degenerative diseases and tissue restoration, as well as to all the potentially chronic inflammatory imbalances, which underpin normal and pathophysiological ageing, and disease [Gorgoulis & Halazonetis, Curr Opin Cell Biol 2010; Chen Q M, Ann N Y Acad Sci 2000; Rodier & Campisi, J Cell Biol 2011; Bartkova J et al, Nature 2006; Halazonetis et al, Science 2008; Liontos et al, Cancer Res 2007; Liontos et al, Am J Pathol 2009]. Ever since cellular senescence was identified as a tumor suppressor mechanism [Bartkova J et al, Nature 2006; Halazonetis et al, Science 2008; Liontos et al, Cancer Res 2007; Liontos et al, Am J Pathol 2009; Shay & Roninson, Oncogene 2004], and as a marker of ageing, a quest for reliable and convenient senescence biomarkers has been conducted [Collado & Serrano, Nat Rev Cancer 2006].

The reason is that accurate recognition of senescent cells is essential for the thorough study of the role of cellular senescence in the development and progression of tissue homeostasis and neoplasms [de Jesus & Blasco, Circ Res 2012]. Furthermore, senescence is induced by a significant number of widely-used age-enhancing therapies, but the precise significance of senescence to the outcome of currently used treatments, such as degenerative disease therapy, is unclear because of the lack of an easy-in-use biomarker that can be adapted to the requirements of clinico-pathological studies [Dimri et al, Proc Natl Acad Sci USA 1995; Collado & Serrano, Nat Rev Cancer 2006]. Notably, such studies are vastly based on the exploitation of archival histologic samples stored.

The current, most popular biomarker for detecting cellular senescence is senescence-associated β-galactosidase activity (SA-β-gal), for which a biochemical assay is employed that identifies increased activity of lysosomal β-D-galactosidase in senescent cells in conditions of suboptimal pH (pH: 6.0) [Dimri et al, Proc Natl Acad Sci USA 1995; Collado & Serrano, Nat Rev Cancer 2006; U.S. Pat. No. 5,491,069]. SA-β gal is applicable for in vitro and in vivo studies, however, its major limitation is the requirement of fresh/frozen biological material. This technique should be conducted under strictly monitored conditions, always in comparison with a negative control, while the overall stress in cellular systems should be avoided (i.e. serum starvation, confluent cultures which may lead to false-positive results, etc) [Severino et al, Exp Cell Res 2000]. In addition, SA-β-gal does not indicate exclusively senescent cells and is often used in combination with other supplementary techniques [Collado & Serrano, Nat Rev Cancer 2006]. Moreover, tissue samples should be directly frozen in liquid nitrogen and processed as soon as possible to retain enzymatic activity [Rodier & Campisi, J Cell Biol 2011; Debacq-Chainiaux F et al, Nat Protoc 2009]. Hence, as SA-β-gal is not applicable to archival material and its use is rather laborious, many researchers have attempted to establish more convenient senescence biomarkers [Collado & Serrano, Nat Rev Cancer 2006; Binet et al, Cancer Res 2009].

A novel method that bypasses these restrictive disadvantages has recently been developed [Georgakopoulou et al, Aging (Albany N.Y.) 2013].

Specifically, we demonstrated the specific use of lipofuscin staining with Sudan Black B (SBB) as a reliable alternative to SA-β-gal biomarker with the advantage of applicability to archival tissue [Georgakopoulou et al, Aging (Albany N.Y.) 2013]. Lipofuscin (also termed as a "wear and tear" substance, "age-pigment" and "age fluorophore") is a by-product of "aged" cells [Jung et al, Methods Mol Biol 2010; Jung et al, Ann N Y Acad Sci 2007]. Lipofuscin is considered a "hallmark of ageing" because its concentration increases with age and is inversely correlated with expected lifespan, especially in post-mitotic and stable cells [Brunk & Terman, Free Radic Biol Med 2002]. Due to its association with aging, it was hypothesized that detection of lipofuscin could be used as an alternative method for identifying senescent cells. Lipofuscin accumulates in the cytosolic compartment of non-dividing cells and mainly in the lysosomes due to its non-soluble and non-degradable nature [Jung et al, Methods Mol Biol 2010; Jung et al, Ann N Y Acad Sci 2007; Hohn et al, Free Radic Biol Med 2010]. It consists of oxidized and cross-linked proteins, lipids and metals (copper and iron) [Jung et al, Ann N Y Acad Sci 2007; Hohn et al, Free Radic Biol Med 2010]. It may be detected with fluorescence microscopy due to its natural autofluorescence [Dowson & Harris, J Microsc 1981] as well as by the use of histochemical techniques [Jung & Grune Methods in Molecular Biology 2010; Charles C, Theory and Practice of Histological Techniques 2002]. The SBB technique is a well-known histochemical stain that has been used for many years for the identification of lipofuscin [Glees & Hasan, Norm Pathol Anat (Stuttg) 1976; Robles L J, Mech Ageing Dev 1978]. In addition, only the SBB stain has the unique property of "masking" the autofluorescence of lipofuscin, so that the latter feature can be used as a control of the method accuracy [Georgakopoulou et al, Aging (Albany N.Y.) 2013]. We have demonstrated that SBB stain can be used as a senescence biomarker [Georgakopoulou et al, Aging (Albany N.Y.) 2013]. To achieve that, we applied SBB in mammalian tissues and cellular systems of both replicative and premature senescence (FIG. 1) in comparison with SA-β-gal in order to test the ability to detect senescent cells and we showed that results of both techniques matched. Most importantly the SBB could identify senescent cells in paraffin-embedded tissues [Georgakopoulou et al, Aging (Albany N.Y.) 2013]. This property opens a wide horizon of potential applications in various fields of basic and clinical research, including diagnostics, as it allows the exploitation of archival material for the purposes of cellular senescence studies.

The SBB stain is a lipophilic molecule that shows high affinity for the lipid compartment of lipofuscin. The dye is diluted in ethanol but is transferred to lipofuscin, when immobilized tissues/cells are immersed in SBB/ethanol solutions, due to its high lipophilicity (more soluble to lipidic parts of lipofuscin than to ethanol) [Georgakopoulou et al, Aging (Albany N.Y.) 2013]. The positive lipofuscin stain reveals blue to black intracellular granules in cellular systems and frozen tissues [Georgakopoulou et al, Aging (Albany N.Y.) 2013], and brown to black granules in paraffin embedded tissues [Georgakopoulou et al, Aging (Albany N.Y.) 2013]. Results from our group have extensively shown that the SBB-specific lipofuscin stain is highly selective for the detection of senescent cells and this may be due to the fact that lipofuscin presence is causally related to the phenomenon of cellular senescence [Georgakopoulou et al, Aging (Albany N.Y.) 2013]. The above technique shows excellent results, it is easily applicable and it has been evaluated in various cellular systems and frozen tissues [Georgakopoulou et al, Aging (Albany N.Y.) 2013]. However, when it comes to histological samples embedded in paraffin, the identification of SBB-positive granules requires a very high magnification, such as 630×, calling for a highly skilled and experienced researcher to perform the evaluation [Georgakopoulou et al, Aging (Albany N.Y.) 2013]. The inevitable presence of smaller granules in paraffin-embedded tissue could be possibly attributed to partial lipid striping of the lipofuscin molecule during the preparation of samples (deparaffinisation). In addition, the necessity to have saturated ethanol-SBB solutions to achieve optimal performance for this staining process imposes practical difficulties during its application.

What is needed is new chemical compounds that possess the same ability of SBB to react specifically with lipofuscin and as such reveal the presence of senescent cells as single ones or in mixed cell populations with greater sensitivity. These compounds should ideally have a high solubility in ethanol.

SUMMARY

The present invention relates to the design and de novo synthesis, using simple molecules, of novel chemical compounds that possess structural similarity to the dye Sudan Black B (SBB). The newly synthesized compounds possess an appropriate substituent, such as a hydroxyl group, a carboxyl group, a primary amino group or a secondary amino group, that confer to the new derivatives higher solubility in ethanol compared to SBB.

The novel chemical compounds are used for the detection of senescent cells that are single or in mixed cell populations through reacting with lipofuscin in a similar manner to the SBB histochemical dye, but with improved performance.

Thus, in one aspect, there is provided a compound, or a salt or solvate thereof, as defined herein.

In a second aspect there is provided a process for preparation of the compounds as defined herein.

In another aspect, there is provided the use of a compound, or a salt or solvate thereof, as defined herein, for the detection of senescent cells.

In another aspect, there is provided the use of a compound, or a salt or solvate thereof, as defined herein, for the detection of single senescent cells or senescent cells in mixed cell populations.

In another aspect, there is provided the use of a compound, or a salt or solvate thereof, as defined herein, for the detection of senescent cells.

In another aspect, there is provided a method of detecting senescence by contacting a compound, or a salt or solvate thereof, as defined herein, with a sample of single or mixed cells, in the presence of lipofuscin.

In a further aspect, there is provided a kit as defined herein.

Features, including optional, suitable, and preferred features in relation to one aspect of the invention may also be features, including optional, suitable and preferred features in relation to any other aspects of the invention.

DETAILED DESCRIPTION

Definitions

Figure 1:
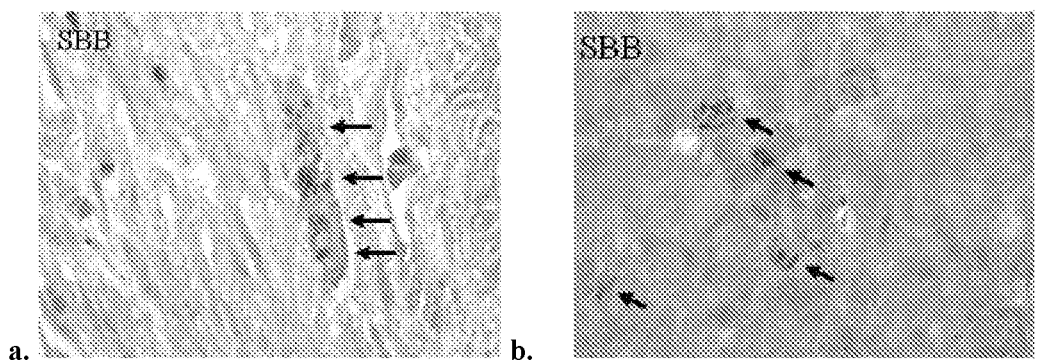
FIG. 1. Detection of senescent cells with SBB histochemical staining in tissue sections from (a) irradiated human laryngeal tumors and (b) mouse lung adenomas, with established presence of senescent cells. Arrows depict stained senescent cells.

Unless otherwise stated, the following terms used in the specification and claims have the following meanings set out below.

In this specification the term "alkyl" includes both straight and branched chain alkyl groups. References to individual alkyl groups such as "propyl" are specific for the straight chain version only and references to individual branched chain alkyl groups such as "isopropyl" are specific for the branched chain version only. For example, "(1-6C)alkyl" includes (1-4C)alkyl, (1-3C)alkyl, propyl, isopropyl and t butyl. A similar convention applies to other radicals, for example "phenyl(1-6C)alkyl" includes phenyl(1-4C)alkyl, benzyl, 1 phenylethyl and 2 phenylethyl.

The term "(m-nC)" or "(m-nC) group" used alone or as a prefix, refers to any group having m to n carbon atoms.

The term "aryl" means a cyclic or polycyclic aromatic ring having from 5 to 12 carbon atoms. The term aryl includes both monovalent species and divalent species. Examples of aryl groups include, but are not limited to, phenyl, biphenyl, naphthyl and the like. In particular embodiment, an aryl is phenyl.

The term "aryl(1-10C)alkyl" means an aryl group covalently attached to a (1-10C)alkylene group, both of which are defined herein. Examples of aryl-(1-10C)alkyl groups include benzyl, phenylethyl, and the like.

The term "optionally substituted" refers to either groups, structures, or molecules that are substituted and those that are not substituted. The term "wherein a group optionally substituted" suitably means that (any) one of the hydrogen radicals of the group is substituted by any suitable functional group. For example, the term "optionally substituted" may refer to the optional substitution by one or more of the following groups from halo, trifluoromethyl, trifluoromethoxy, amino, cyano, hydroxy, carboxy, carbamoyl, sulphamoyl, aryl, heteroaryl, (1-6C)alkyl, (3-8C)cycloalkyl or (1-6C)alkoxy.

Compounds of the Invention

We propose the design and de novo synthesis—i.e. the generation from the beginning, using simple molecules—of chemical compounds that can react specifically with lipofuscin, in a similar fashion to SBB and improved sensitivity, within senescent cells only.

The SBB compound ($C_{29}H_{24}N_6$) shows high stability due to its extended aromatic system and, hence, its targeted chemical modification requires the de novo synthesis, starting from simple molecules, for the preparation of the new desired compounds. The newly synthesized derivatives possess an appropriate substituent, such as a hydroxyl group, a carboxyl group, a primary amino group or a secondary amino group, that confer to the new derivatives higher solubility in ethanol compared to SBB.

Thus, the new compounds are of general formula (1) or (2)

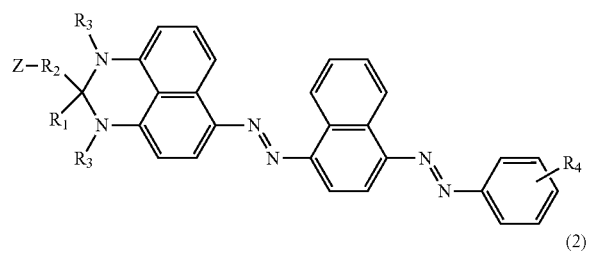

(1)

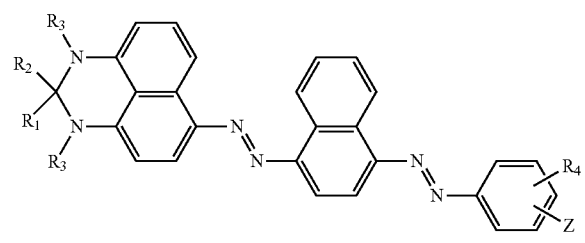

(2)

wherein $R_1$ and $R_2$ are each independently selected from:
i) hydrogen, with the proviso that $R_2$ is not hydrogen in general structure (1) above and only one of $R_1$ and $R_2$ can be hydrogen in general structure (2) above.
ii) an optionally substituted (1-10C)alkyl group;
iii) an optionally substituted aryl group;
iv) an optionally substituted (1-10C)alkyl-aryl group;
v) an optionally substituted aryl-(1-10C)alkyl group; or
vi) $R_1$ and $R_2$ are linked so as to form part of a spiranic cycloalkane group, selected from cyclopentyl, cyclohexyl, cycloheptyl, cyclooctyl, cyclononyl or adamantanyl;

$R_3$ is hydrogen or (1-10C)alkyl group;

$R_4$ is hydrogen, or one or more of the following substituents:
i) a halogen selected from F, Cl, Br and I;
ii) $NO_2$;
iii) $CF_3$;
iv) $SCH_3$;
v) an optionally substituted (1-5C)alkyl group;
vi) a (1-10C)alkoxy group which optionally comprises one or more heteroatoms; and Z is either $Z_1$ or —Ar—$Z_1$— and $Z_1$ is selected from OH, $NH_2$, $O(CH_2)_nCH_2OH$, $(CH_2)_qOH$ or COOH, wherein n is an integer selected from 1 to 9, and wherein q is an integer selected from 1 to 4, and wherein Ar is an aryl group optionally substituted with one or more of the following substituents halogen, (1-6C)alkyl, (1-6C)alkenyl or (1-5C)alkoxy.

Particular compounds of the present invention include, for example, compounds of general formula (1) or (2) defined above, or salts and/or solvates thereof, wherein, unless otherwise stated, each of $R_1$, $R_2$, $R_3$, $R_4$, Z and any associated substituent groups has any of the meanings defined hereinbefore or in any of paragraphs (1) to (19) hereinafter:

(1) $R_1$ and $R_2$ are each independently selected from:
i) hydrogen, provided that at least one of $R_1$, $R_2$ is other than hydrogen;
ii) an optionally substituted (1-8C)alkyl group;
iii) an optionally substituted aryl group;
iv) an optionally substituted (1-8C)alkyl-aryl group;
v) an optionally substituted aryl-(1-8C)alkyl group; or
vi) $R_1$ and $R_2$ are linked so as to form part of a spiranic cycloalkane group, selected from cyclopentyl, cyclohexyl, cycloheptyl, cyclooctyl, cyclononyl or adamantanyl;

(2) $R_1$ and $R_2$ are each independently selected from:
i) hydrogen, provided that at least one of $R_1$, $R_2$ is other than hydrogen;
ii) an optionally substituted (1-8C)alkyl group;
iii) an optionally substituted aryl group;
iv) an optionally substituted (1-8C)alkyl-aryl group; or
v) an optionally substituted aryl-(1-8C)alkyl group;

(3) $R_1$ and $R_2$ are each independently selected from:
i) hydrogen, provided that at least one of $R_1$, $R_2$ is other than hydrogen;
ii) an optionally substituted (1-4C)alkyl group;
iii) an optionally substituted aryl group;
iv) an optionally substituted (1-4C)alkyl-aryl group; or
v) an optionally substituted aryl-(1-4C)alkyl group;

(4) $R_1$ and $R_2$ are each independently selected from:
i) hydrogen, provided that at least one of $R_1$, $R_2$ is other than hydrogen;
ii) a (1-4C)alkyl group;
iii) an aryl group;
iv) a (1-4C)alkyl-aryl group; or
v) an aryl-(1-4C)alkyl group;

(5) $R_1$ and $R_2$ are each independently selected from:
   i) hydrogen, provided that at least one of $R_1$, $R_2$ is other than hydrogen;
   ii) an optionally substituted (1-4C)alkyl group; or
   iii) an optionally substituted aryl group;
(6) $R_1$ and $R_2$ are each independently selected from:
   i) hydrogen, provided that at least one of $R_1$, $R_2$ is other than hydrogen;
   ii) a (1-4C)alkyl group (e.g. methyl); or
   iii) a phenyl group;
(7) $R_3$ is hydrogen or (1-8C)alkyl group;
(8) $R_3$ is hydrogen or (1-4C)alkyl group (e.g. methyl);
(9) $R_3$ is hydrogen;
(10) $R_4$ is hydrogen, or one or more of the following substituents:
   i) a halogen selected from F, Cl, Br and I;
   ii) $NO_2$;
   iii) $CF_3$;
   iv) $SCH_3$;
   v) a (1-5C)alkyl group; or
   vi) a (1-10C)alkoxy group;
(11) $R_4$ is hydrogen, or one or more of the following substituents:
   i) a halogen selected from F, Cl, Br and I, preferably F or Cl;
   ii) $NO_2$;
   iii) $CF_3$;
   iv) a (1-5C)alkyl group (e.g. methyl); or
   v) a (1-5C)alkoxy group (e.g. methoxy);
(12) $R_4$ is hydrogen;
(13) Z is either $Z_1$ or Ar—$Z_1$, and $Z_1$ is selected from —OH, —$NH_2$, —O($CH_2$)$_n$$CH_2$OH, —($CH_2$)$_q$OH or —COOH, wherein n is an integer selected from 1 to 4, wherein q is an integer selected from 1 to 4, and wherein Ar is an aryl group optionally substituted with one or more of the following substituents halogen, (1-4C)alkyl, (1-4C)alkenyl or (1-4C)alkoxy;
(14) Z is either $Z_1$ or Ar—$Z_1$, and $Z_1$ is selected from —OH, —$NH_2$, —O($CH_2$)$_n$$CH_2$OH or —($CH_2$)$_q$OH, wherein n is an integer selected from 1 to 4, wherein q is an integer selected from 1 to 4, and wherein Ar is an aryl group optionally substituted with one or more of the following substituents halogen, (1-4C)alkyl, (1-4C)alkenyl or (1-4C)alkoxy;
(15) Z is either $Z_1$ or Ar—$Z_1$, and $Z_1$ is selected from —OH, —$NH_2$, —O($CH_2$)$_n$$CH_2$OH or —($CH_2$)$_q$OH, wherein n is an integer selected from 1 to 4, wherein q is an integer selected from 1 to 4, and wherein Ar is an aryl group;
(16) Z is either $Z_1$ or Ar—$Z_1$, and $Z_1$ is selected from —OH or —$NH_2$, wherein Ar is an aryl group optionally substituted with one or more of the following substituents halogen, (1-4C)alkyl, (1-4C)alkenyl or (1-4C)alkoxy;
(17) Z is either $Z_1$ or Ar—$Z_1$, and $Z_1$ is selected from —OH or —$NH_2$, wherein Ar is an aryl group;
(18) Z is either $Z_1$ or Ar—$Z_1$, and $Z_1$ is selected from —OH or —$NH_2$, wherein Ar is a phenyl group;
(19) Z is either $Z_1$ or Ar—$Z_1$, and $Z_1$ is —OH and Ar is a phenyl group.

Suitably, $R_1$ and $R_2$ are as defined in any one of paragraphs (1) to (6) above. Most suitably, $R_1$ and $R_2$ are as defined in paragraph (6) above.

Suitably, $R_3$ is as defined in any one of paragraphs (7) to (9) above.

Suitably, $R_4$ is as defined in any one of paragraphs (10) to (12) above.

Suitably, Z is as defined in any one of paragraphs (13) to (19) above. Most suitably, Z is as defined in paragraph (19) above.

In an embodiment, the present invention provides a compound of general structure (1).

In another embodiment, the present invention provides a compound of general structure (2).

In a particular embodiment, the compound of the present invention is not 2-(2-Methyl-6-((E)-(4-((E)-phenyldiazenyl)naphthalen-1-yl)diazenyl)-2,3-dihydro-1H-perimidin-2-yl)ethanol, the structure of which is given below:

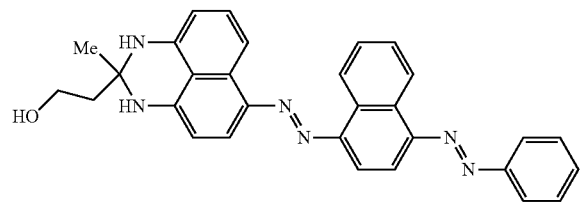 [SMILES: CC1(CCO)Nc2cccc3c(/N=N/c4ccc(/N=N/c5ccccc5)c5ccccc45)ccc(c23)N1]

Particular Embodiments

In a particular group of compounds of general formulae (1) or (2), $R_3$ is hydrogen, i.e. the compounds have the structural formula 1b or 2b (sub-definitions of general formula (1) and (2)) shown below:

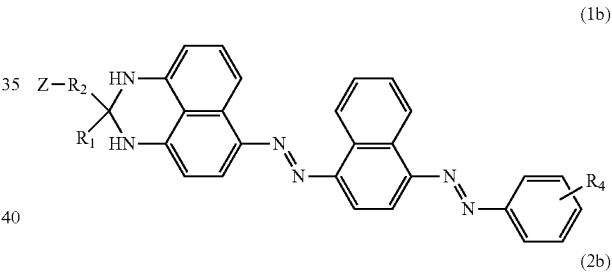

(1b)

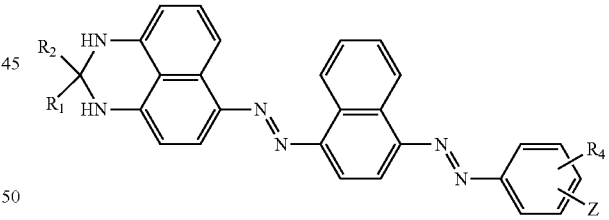

(2b)

wherein, $R_1$, $R_2$, $R_4$ and Z are as defined hereinabove.

In an embodiment of the compounds of Formula 1b and 2b:
   $R_1$ and $R_2$ are as defined in any one of paragraphs (1) to (6) above;
   $R_4$ is as defined in any one of paragraphs (10) to (12) above; and
   Z is as defined in any one of paragraphs (13) to (19) above.

In another embodiment of the compounds of Formula 1b and 2b:
   $R_1$ and $R_2$ are as defined in paragraph (6) above;
   $R_4$ is as defined in paragraph (12) above; and
   Z is as defined in paragraph (19) above.

Compounds of General Structure (3)

In one embodiment, the appropriate substituent, preferably a hydroxyl group, has been introduced to the 2,3-dihydro-1H-perimidine ring of the SBB compound, leading to compounds of the general structure (3)

(3)

wherein
- $R_1$ is a (1-10C)alkyl;
- $R_2$ is selected from:
  i) an optionally substituted (1-8C)alkyl group;
  ii) an optionally substituted aryl group; or
  iii) an optionally substituted (1-5C)alkyl-aryl group;
- $R_3$ is hydrogen or (1-10C)alkyl group; and
- $R_4$ is hydrogen, or one or more of the following substituents:
  i) a halogen selected from F, Cl, Br and I;
  ii) $NO_2$;
  iii) $CF_3$,
  iv) $SCH_3$;
  v) an optionally substituted (1-5C)alkyl group; or
  vi) a (1-10C)alkoxy group which optionally comprises one or more heteroatoms.

In a particular embodiment, the compound of the general structure (3) is not 2-(2-Methyl-6-((E)-(4-((E)-phenyldiazenyl)naphthalen-1-yl)diazenyl)-2,3-dihydro-1H-perimidin-2-yl)ethanol In an embodiment of the compounds of the general structure (3):
- $R_1$ is a (1-4C)alkyl group;
- $R_2$ is a (1-8C)alkyl group or an optionally substituted aryl group;
- $R_3$ is hydrogen; and
- $R_4$ is hydrogen, or one or more of the following substituents:
  i) a halogen selected from F or Cl;
  ii) $NO_2$;
  iii) $CF_3$,
  iv) a (1-5C)alkyl group (e.g. methyl); or
  v) a (1-5C)alkoxy group (e.g. methoxy).

In another embodiment of the compounds of the general structure (3):
- $R_1$ is a (1-4C)alkyl group;
- $R_2$ is a methyl group or a phenyl group;
- $R_3$ is hydrogen; and
- $R_4$ is hydrogen, or one or more of the following substituents:
  i) a halogen selected from F or Cl;
  ii) $NO_2$;
  iii) $CF_3$,
  iv) a (1-5C)alkyl group (e.g. methyl); or
  v) a (1-5C)alkoxy group (e.g. methoxy).

In yet another embodiment of the compounds of the general structure (3):
- $R_1$ is a (1-4C)alkyl group (e.g. methyl);
- $R_2$ is a (1-4C)alkyl group (e.g. methyl) or an aryl group (e.g. phenyl); and
- $R_3$ and $R_4$ are hydrogen; and Compounds of General Structure (4)

In another embodiment the appropriate substituent, preferably a hydroxyl group or the $O(CH_2)_nCH_2OH$ group where n is 1 up to 9, has been introduced to an aryl group present at position 2 of the 2,3-dihydro-1H-perimidine group of the SBB compound, leading to compounds of the general structure (4)

(4)

wherein
- x is an integer selected from 0 or 1;
- n is an integer selected from 1 to 9;
- $R_4$ is hydrogen, or one or more of the following substituents:
  i) a halogen selected from F, Cl, Br and I;
  ii) $NO_2$;
  iii) $CF_3$,
  iv) $SCH_3$;
  v) an optionally substituted (1-5C)alkyl group; or
  vi) a (1-10C)alkoxy group which optionally comprises one or more heteroatoms; and
- $R_5$ is hydrogen, or one or more of the following substituents:
  i) a halogen selected from F, Cl, Br and I;
  ii) a (1-6C)alkyl or (1-6C)alkenyl group; or
  iii) a (1-5C)alkoxy group.

In an embodiment of the compounds of the general structure (4):
x is an integer selected from 0 or 1;
n is an integer selected from 1 to 4;
$R_4$ is hydrogen, or one or more of the following substituents:
i) a halogen selected from F or Cl;
ii) $NO_2$;
iii) $CF_3$;
iv) a (1-5C)alkyl group (e.g. methyl); or
v) a (1-5C)alkoxy group (e.g. methoxy);
$R_5$ is hydrogen, or one or more of the following substituents:
i) halogen selected from F, Cl, Br and I;
ii) (1-6C)alkyl group; or
iii) (1-5C)alkoxy group.

In another embodiment of the compounds of the general structure (4):
x is an integer selected from 0 or 1;
n is an integer selected from 1 to 4;
$R_4$ and $R_5$ are hydrogen.

Compounds of General Structure (5)

In yet another embodiment the appropriate substituent, preferably a hydroxyl group or the $O(CH_2)_nCH_2OH$ group where n is 1 up to 9, has been introduced to the position 4 of the end terminal aniline unit of SBB compound, leading to compounds of the general structure (5)

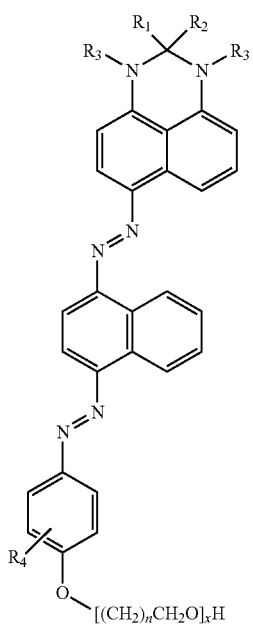

(5)

wherein
x is an integer selected from 0 or 1;
n is an integer selected from 1 to 9;
$R_1$ and $R_2$ are each independently selected from:
i) hydrogen, provided that at least one of $R_1$ and $R_2$ is a substituent group other than hydrogen;
ii) an optionally substituted (1-10C)alkyl group;
iii) an optionally substituted aryl group;
iv) an optionally substituted (1-10C)alkyl-aryl group;
v) an optionally substituted aryl-(1-10C)alkyl group; or
vi) $R_1$ and $R_2$ are linked so as to form part of a spiranic cycloalkane group, selected from cyclopentyl, cyclohexyl, cycloheptyl, cyclooctyl, cyclononyl or adamantanyl;
$R_3$ is hydrogen or (1-10C)alkyl group; and
$R_4$ is hydrogen, or one or more of the following substituents:
i) a halogen selected from F, Cl, Br and I;
ii) $NO_2$;
iii) $CF_3$,
iv) $SCH_3$;
v) an optionally substituted (1-5C)alkyl group; or
vi) a (1-10C)alkoxy group which optionally comprises one or more heteroatoms.

In an embodiment of the compounds of the general structure (5):
x is an integer selected from 0 or 1;
n is an integer selected from 1 to 4;
$R_1$ and $R_2$ are each independently selected from:
i) hydrogen, provided that at least one of $R_1$ and $R_2$ is a substituent group other than hydrogen;
ii) a (1-4C)alkyl group;
iii) an aryl group;
iv) a (1-4C)alkyl-aryl group; or
v) an aryl-(1-4C)alkyl group;
$R_3$ is hydrogen or a (1-4C)alkyl group; and
$R_4$ is hydrogen, or one or more of the following substituents:
i) a halogen selected from F or Cl;
ii) $NO_2$;
iii) $CF_3$,
iv) a (1-5C)alkyl group (e.g. methyl); or
v) a (1-5C)alkoxy group (e.g. methoxy).

In another embodiment of the compounds of the general structure (5):
x is an integer selected from 0 or 1;
n is an integer selected from 1 to 4;
$R_1$ and $R_2$ are independently selected from hydrogen or a (1-4C)alkyl group (e.g. methyl), provided that at least one of $R_1$ and $R_2$ is a substituent group other than hydrogen; and
$R_3$ and $R_4$ are hydrogen.

Compounds of General Structure (6)

In yet another embodiment the appropriate substituent, preferably a hydroxyl group or the $O(CH_2)_nCH_2OH$ group where n is 1 up to 9, has been introduced to the position 3 of the end terminal aniline unit of SBB compound, leading to compounds of the general structure (6).

(6)

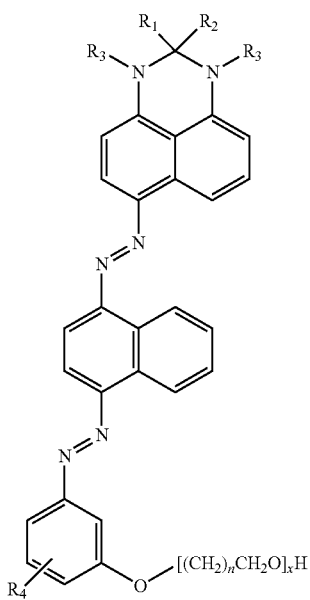

wherein
x is an integer selected from 0 or 1;
n is an integer selected from 1 to 9;
$R_1$ and $R_2$ are each independently selected from:
i) hydrogen, provided that at least one of $R_1$ and $R_2$ is a substituent group other than hydrogen;
ii) an optionally substituted (1-10C)alkyl group;
iii) an optionally substituted aryl group;
iv) an optionally substituted (1-10C)alkyl-aryl group;
v) an optionally substituted aryl-(1-10C)alkyl group; or
vi) $R_1$ and $R_2$ are linked so as to form part of a spiranic cycloalkane group, selected from cyclopentyl, cyclohexyl, cycloheptyl, cyclooctyl, cyclononyl or adamantanyl;
$R_3$ is hydrogen or (1-10C)alkyl group; and
$R_4$ is hydrogen, or one or more of the following substituents:
i) a halogen selected from F, Cl, Br and I;
ii) $NO_2$;
iii) $CF_3$,
iv) $SCH_3$;
v) an optionally substituted (1-5C)alkyl group; or
vi) a (1-10C)alkoxy group which optionally comprises one or more heteroatoms.

In an embodiment of the compounds of the general structure (6):
x is an integer selected from 0 or 1;
n is an integer selected from 1 to 4;
$R_1$ and $R_2$ are each independently selected from:
i) hydrogen, provided that at least one of $R_1$ and $R_2$ is a substituent group other than hydrogen;
ii) a (1-4C)alkyl group;
iii) an aryl group;
iv) a (1-4C)alkyl-aryl group; or
v) an aryl-(1-4C)alkyl group;
$R_3$ is hydrogen or a (1-4C)alkyl group;
$R_4$ is hydrogen, or one or more of the following substituents:
i) a halogen selected from F or Cl;
ii) $NO_2$;
iii) $CF_3$,
iv) a (1-5C)alkyl group (e.g. methyl); or
v) a (1-5C)alkoxy group (e.g. methoxy).

In another embodiment of the compounds of the general structure (6):
x is an integer selected from 0 or 1;
n is an integer selected from 1 to 4;
$R_1$ and $R_2$ are independently selected from hydrogen or a (1-4C)alkyl group (e.g. methyl), provided that at least one of $R_1$ and $R_2$ is a substituent group other than hydrogen; and
$R_3$ and $R_4$ are hydrogen.

Compounds of General Structure (7)

In yet another embodiment the appropriate substituent, preferably the $(CH_2)_qOH$ group where q is 1 up to 4, has been introduced to the position 4 of the end terminal aniline unit of SBB compound, so that an interposition of an alkyl bridge consisting of methylene units between the aniline group of SBB and the hydroxyl group is present, leading to compounds of the general structure (7).

(7)

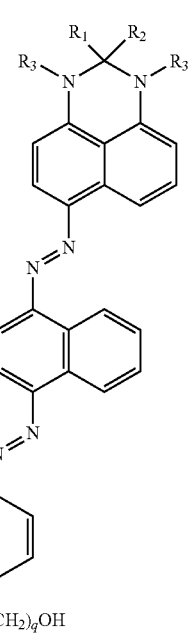

wherein
q is an integer selected from 1 to 4;
$R_1$ and $R_2$ are each independently selected from:
i) hydrogen, provided that at least one of $R_1$ and $R_2$ is a substituent group other than hydrogen;
ii) an optionally substituted (1-10C)alkyl group;
iii) an optionally substituted aryl group;
iv) an optionally substituted (1-10C)alkyl-aryl group;
v) an optionally substituted aryl-(1-10C)alkyl group; or
vi) $R_1$ and $R_2$ are linked so as to form part of a spiranic cycloalkane group, selected from cyclopentyl, cyclohexyl, cycloheptyl, cyclooctyl, cyclononyl or adamantanyl;
$R_3$ is hydrogen or (1-10C)alkyl group; and
$R_4$ is hydrogen, or one or more of the following substituents:
i) a halogen selected from F, Cl, Br and I;
ii) $NO_2$;
iii) $CF_3$,
iv) $SCH_3$;

v) an optionally substituted (1-5C)alkyl group; or vi) a (1-10C)alkoxy group which optionally comprises one or more heteroatoms.

In an embodiment of the compounds of the general structure (7):

q is an integer selected from 1 to 4;

$R_1$ and $R_2$ are each independently selected from:
i) hydrogen, provided that at least one of $R_1$ and $R_2$ is a substituent group other than hydrogen;
ii) a (1-4C)alkyl group;
iii) an aryl group;
iv) a (1-4C)alkyl-aryl group; or
v) an aryl-(1-4C)alkyl group;

$R_3$ is hydrogen or a (1-4C)alkyl group;

$R_4$ is hydrogen, or one or more of the following substituents:
i) a halogen selected from F or Cl;
ii) $NO_2$;
iii) $CF_3$,
iv) a (1-5C)alkyl group (e.g. methyl); or
v) a (1-5C)alkoxy group (e.g. methoxy).

In an embodiment of the compounds of the general structure (7):

q is an integer selected from 1 to 4;

$R_1$ and $R_2$ are independently selected from hydrogen or a (1-4C)alkyl group (e.g. methyl), provided that at least one of $R_1$ and $R_2$ is a substituent group other than hydrogen; and $R_3$ and $R_4$ are hydrogen.

Compounds of General Structure (8)

In yet another embodiment the appropriate substituent, preferably the $(CH_2)_qOH$ group where q is 1 up to 4, has been introduced to the position 3 of the end terminal aniline unit of SBB compound, so that an interposition of an alkyl bridge consisting of methylene units between the aniline group of SBB and the hydroxyl group is present, leading to compounds of the general structure (8)

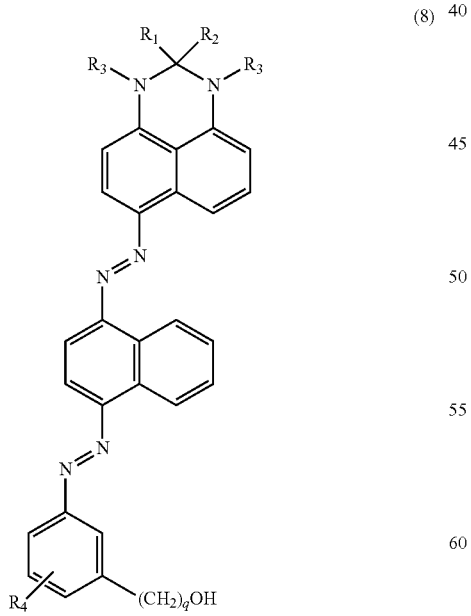

(8)

wherein q is an integer selected from 1 to 4;

$R_1$ and $R_2$ are each independently selected from:

i) hydrogen, provided that at least one of $R_1$ and $R_2$ is a substituent group other than hydrogen;

ii) an optionally substituted (1-10C)alkyl group;

iii) an optionally substituted aryl group;

iv) an optionally substituted (1-10C)alkyl-aryl group;

v) an optionally substituted aryl-(1-10C)alkyl group; or vi) $R_1$ and $R_2$ are linked so as to form part of a spiranic cycloalkane group, selected from cyclopentyl, cyclohexyl, cycloheptyl, cyclooctyl, cyclononyl or adamantanyl;

$R_3$ is hydrogen or (1-10C)alkyl group; and $R_4$ is hydrogen, or one or more of the following substituents:

i) a halogen selected from F, Cl, Br and I;

ii) $NO_2$;

iii) $CF_3$, iv) $SCH_3$;

v) an optionally substituted (1-5C)alkyl group; or vi) a (1-10C)alkoxy group which optionally comprises one or more heteroatoms.

In an embodiment of the compounds of the general structure (8):

q is an integer selected from 1 to 4;

$R_1$ and $R_2$ are each independently selected from:

i) hydrogen, provided that at least one of $R_1$ and $R_2$ is a substituent group other than hydrogen;

ii) a (1-4C)alkyl group;

iii) an aryl group;

iv) a (1-4C)alkyl-aryl group; or v) an aryl-(1-4C)alkyl group;

$R_3$ is hydrogen or a (1-4C)alkyl group;

$R_4$ is hydrogen, or one or more of the following substituents:

i) a halogen selected from F or Cl;

ii) $NO_2$;

iii) $CF_3$, iv) a (1-5C)alkyl group (e.g. methyl); or v) a (1-5C)alkoxy group (e.g. methoxy).

In an embodiment of the compounds of the general structure (8):

q is an integer selected from 1 to 4;

$R_1$ and $R_2$ are independently selected from hydrogen or a (1-4C)alkyl group (e.g. methyl), provided that at least one of $R_1$ and $R_2$ is a substituent group other than hydrogen; and $R_3$ and $R_4$ are hydrogen.

Particular compounds of general formula (1) or (2) include any of the compounds exemplified in the present application, or a salt or solvate thereof, and, in particular, any of the following:

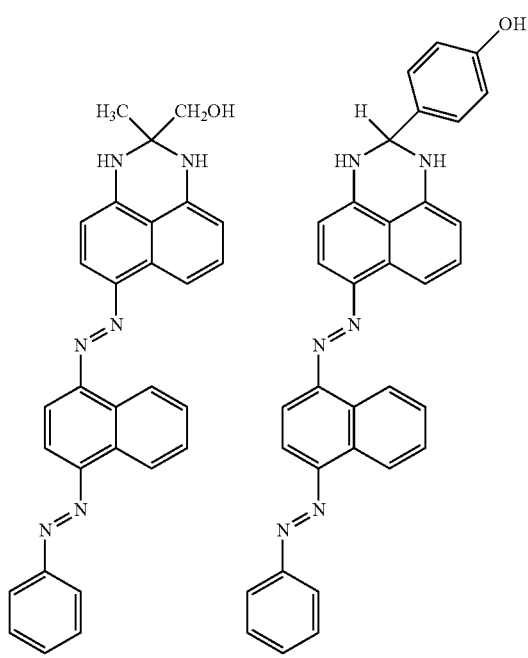
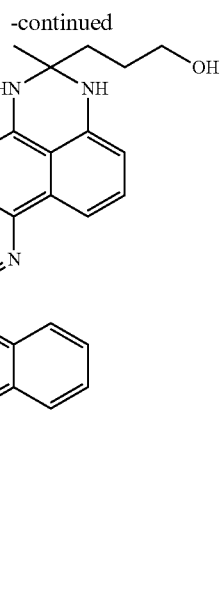
Further compounds of general formula (1) or (2) include any of the compounds exemplified in the present application, or a salt or solvate thereof, and, in particular, any of the following:
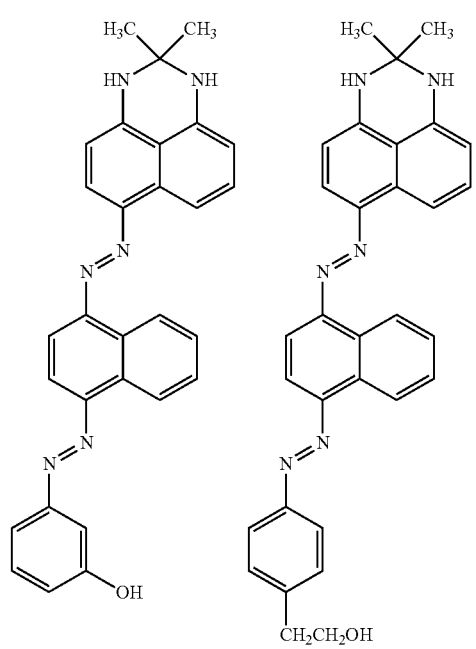
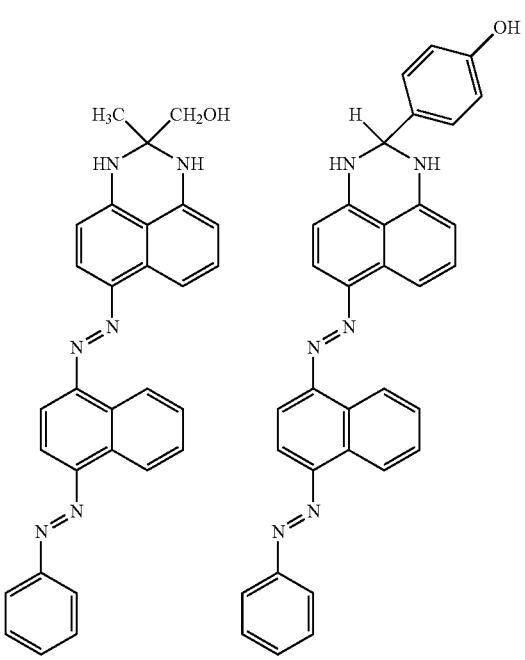

-continued

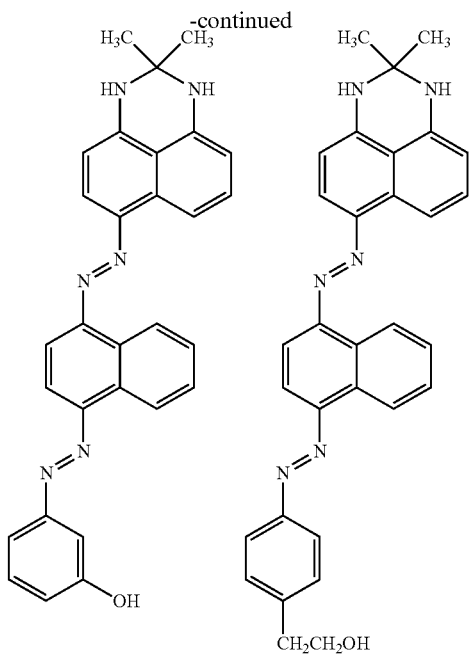

In a particular embodiment, the compound of the present invention is:

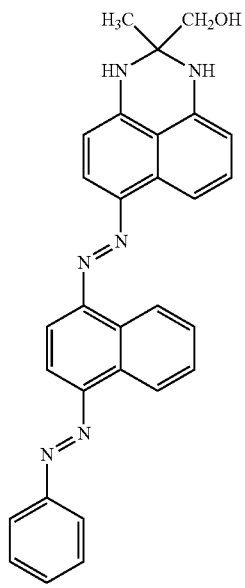 [SMILES: CC1(CO)Nc2cccc3c(/N=N/c4ccc(/N=N/c5ccccc5)c5ccccc45)ccc(c23)N1]

The various functional groups and substituents making up the compounds of general formula 1 or 2 (or compounds of sub-formulae (3) to (8)) are typically chosen such that the molecular weight of the compound of general formula 1 or 2 does not exceed 1000. More usually, the molecular weight of the compound will be less than 900, for example less than 800, or less than 700, or less than 600.

A suitable salt of a compound of general formula 1 or 2 (or compounds of sub-formulae (3) to (8)) is, for example, an acid-addition salt of a compound of the invention which is sufficiently basic, for example, an acid-addition salt with, for example, an inorganic or organic acid, for example hydrochloric, hydrobromic, sulfuric, phosphoric, trifluoro-acetic, formic, citric methane sulfonate or maleic acid. In addition, a suitable pharmaceutically acceptable salt of a cytochrome be inhibitor of the invention which is sufficiently acidic is an alkali metal salt, for example a sodium or potassium salt, an alkaline earth metal salt, for example a calcium or magnesium salt, an ammonium salt or a salt with an organic base which affords a pharmaceutically acceptable cation, for example a salt with methylamine, dimethylamine, trimethylamine, piperidine, morpholine or tris-(2-hydroxyethyl)amine.

Compounds that have the same molecular formula but differ in the nature or sequence of bonding of their atoms or the arrangement of their atoms in space are termed "isomers". Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn-Ingold-Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The compounds of general formula 1 or 2 (or compounds of sub-formulae (3) to (8)) of this invention may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see discussion in Chapter 4 of "Advanced Organic Chemistry", 4th edition J. March, John Wiley and Sons, New York, 2001), for example by synthesis from optically active starting materials or by resolution of a racemic form. Some of the compounds of the invention may have geometric isomeric centres (E- and Z-isomers). It is to be understood that the present invention encompasses all optical, diastereoisomers and geometric isomers and mixtures thereof that possess β-lactamase inhibitory activity.

The present invention also encompasses compounds of general formula 1 or 2 (or compounds of sub-formulae (3) to (8)) which comprise one or more isotopic substitutions. For example, H may be in any isotopic form, including $^1H$, $^2H(D)$, and $^3H$ (T); C may be in any isotopic form, including $^{12}C$, $^{13}C$, and $^{14}C$; and O may be in any isotopic form, including $^{16}O$ and $^{18}O$; and the like.

It is also to be understood that certain compounds of general formula 1 or 2 (or compounds of sub-formulae (3) to (8)) may exist in solvated as well as unsolvated forms such as, for example, hydrated forms. It is to be understood that the invention encompasses all such solvated forms that possess β-lactamase inhibitory activity.

Compounds of general formula 1 or 2 (or compounds of sub-formulae (3) to (8)) may also exist in a number of different tautomeric forms and references to compounds of general formula 1 or 2 (or compounds of sub-formulae (3) to (8)) include all such forms. For the avoidance of doubt, where a compound can exist in one of several tautomeric forms, and only one is specifically described or shown, all others are nevertheless embraced the structural formula of general formula 1 or 2 (or compounds of sub-formulae (3) to (8)). Examples of tautomeric forms include keto-, enol-, and enolate-forms, as in, for example, the following tautomeric pairs: keto/enol (illustrated below), imine/enamine, amide/imino alcohol, amidine/amidine, nitroso/oxime, thioketone/enethiol, and nitro/aci-nitro.

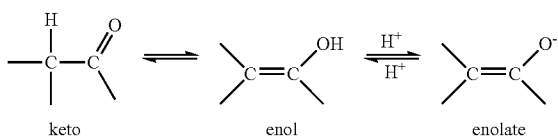

keto          enol          enolate

Compounds of general formula 1 or 2 (or compounds of sub-formulae (3) to (8)) containing an amine function may also form N-oxides. A reference herein to a compounds of general formula 1 or 2 (or compounds of sub-formulae (3) to (8)) that contains an amine function also includes the N-oxide. Where a compounds of general formula 1 or 2 (or compounds of sub-formulae (3) to (8)) contains several amine functions, one or more than one nitrogen atom may be oxidised to form an N-oxide. Particular examples of N-oxides are the N-oxides of a tertiary amine or a nitrogen atom of a nitrogen-containing heterocycle. N-Oxides can be formed by treatment of the corresponding amine with an oxidizing agent such as hydrogen peroxide or a per-acid (e.g. a peroxycarboxylic acid), see for example *Advanced Organic Chemistry*, by Jerry March, 4$^{th}$ Edition, Wiley Interscience. More particularly, N-oxides can be made by the procedure of L. W. Deady (*Syn. Comm.* 1977, 7, 509-514) in which the amine compound is reacted with m-chloroperoxybenzoic acid (mCPBA), for example, in an inert solvent such as dichloromethane.

Synthesis

The compounds of the present invention can be prepared by any suitable technique known in the art. Particular processes for the preparation of these compounds are described further in the accompanying examples.

In the description of the synthetic methods described herein and in any referenced synthetic methods that are used to prepare the starting materials, it is to be understood that all proposed reaction conditions, including choice of solvent, reaction atmosphere, reaction temperature, duration of the experiment and workup procedures, can be selected by a person skilled in the art.

It is understood by one skilled in the art of organic synthesis that the functionality present on various portions of the molecule must be compatible with the reagents and reaction conditions utilised.

It will be appreciated that during the synthesis of the compounds of the invention in the processes defined herein, or during the synthesis of certain starting materials, it may be desirable to protect certain substituent groups to prevent their undesired reaction. The skilled chemist will appreciate when such protection is required, and how such protecting groups may be put in place, and later removed.

For examples of protecting groups see one of the many general texts on the subject, for example, 'Protective Groups in Organic Synthesis' by Theodora Green (publisher: John Wiley & Sons). Protecting groups may be removed by any convenient method described in the literature or known to the skilled chemist as appropriate for the removal of the protecting group in question, such methods being chosen so as to effect removal of the protecting group with the minimum disturbance of groups elsewhere in the molecule.

Thus, if reactants include, for example, groups such as amino, carboxy or hydroxy it may be desirable to protect the group in some of the reactions mentioned herein.

By way of example, a suitable protecting group for an amino or alkylamino group is, for example, an acyl group, for example an alkanoyl group such as acetyl, an alkoxycarbonyl group, for example a methoxycarbonyl, ethoxycarbonyl or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed by, for example, hydrolysis with a suitable base such as an alkali metal hydroxide, for example lithium or sodium hydroxide. Alternatively an acyl group such as a tert-butoxycarbonyl group may be removed, for example, by treatment with a suitable acid as hydrochloric, sulfuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium, sodium hydroxide or ammonia. Alternatively an arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a t-butyl group which may be removed, for example, by treatment with an acid, for example an organic acid such as trifluoroacetic acid, or for example a benzyl group which may be removed, for example, by hydrogenation over a catalyst such as palladium-on-carbon.

Resins may also be used as a protecting group.

The methodology employed to synthesise a compound of general formula 1 or 2 will vary depending on the nature of $R_1$, $R_2$, $R_3$, $R_4$, Z and any substituent groups associated therewith. Suitable processes for their preparation are described further in the accompanying Examples.

In certain embodiments, the compounds of the present invention (i.e. the compounds of general formula (1) and (2)) are prepared by one of the two different synthetic approaches that follow.

In the first approach, a compound of formula A, as shown below:

is reacted with a with a compound of formula X, shown below:

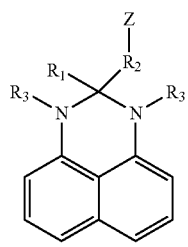

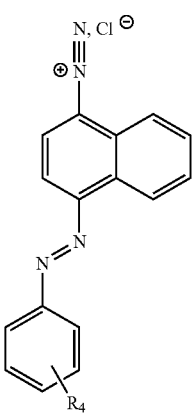

to yield of compound of general formula (1), wherein Z and $R_1$ to $R_4$ are as defined hereinabove.

In a second approach, a compound of formula B, shown below:

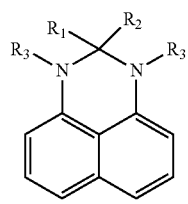

is reacted with a compound of formula Y, shown below:

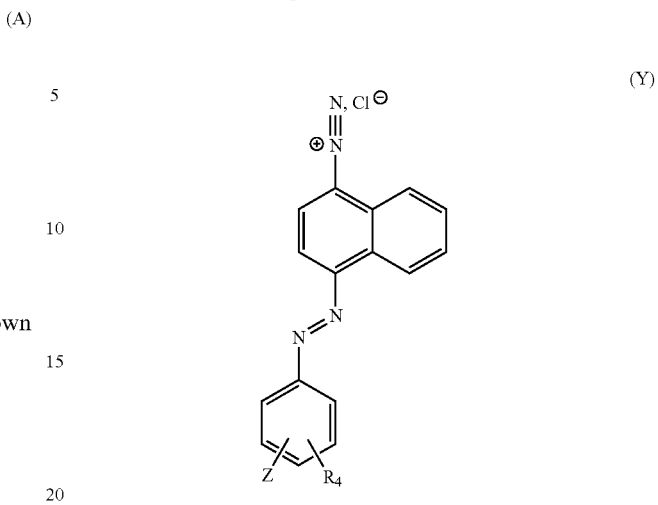

to yield of compound of general formula (2), wherein Z and $R_1$ to $R_4$ are as defined hereinabove.

Thus, concerning the synthesis of the aforementioned compounds, it will be appreciated that these may be prepared according to the synthetic methodology shown in Schemes 3.1 up to 3.8.

More specifically, for the synthesis of compounds that belong to the general formula (3) 8-amino-1-naphthylamine can be used as starting material and upon reaction with the substituted hydroxy ketones will be converted to modified 2,2-substituted-2,3-dihydro-1H-perimidines (Scheme 3.1) [Zhang & Zhang, Synth Comm 2007; Farrand L D et al Merck Patent GMBH Wo 2014/111112 A1]. The bis alkyl substituted perimidines at nitrogens 1 and 3 can be prepared upon treatment with the corresponding alkyl bromide under basic conditions. These compounds can be used as substrates for the electrophilic addition of suitably substituted diazotized amino-derivatives resulting from the coupling of diazotized substituted aniline with 1-naphthylamine. The electrophilic aromatic substitution affords two regio-isomers (6- or 4-substituted derivatives) that can be separated through an appropriate method, for example with column chromatography.

Scheme 3.1 Synthesis of compounds of the general formula (3).

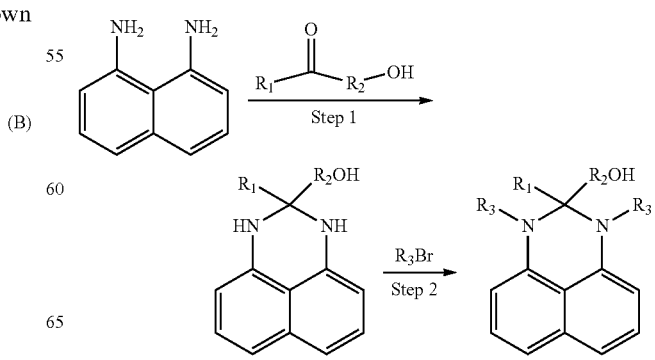

25

-continued

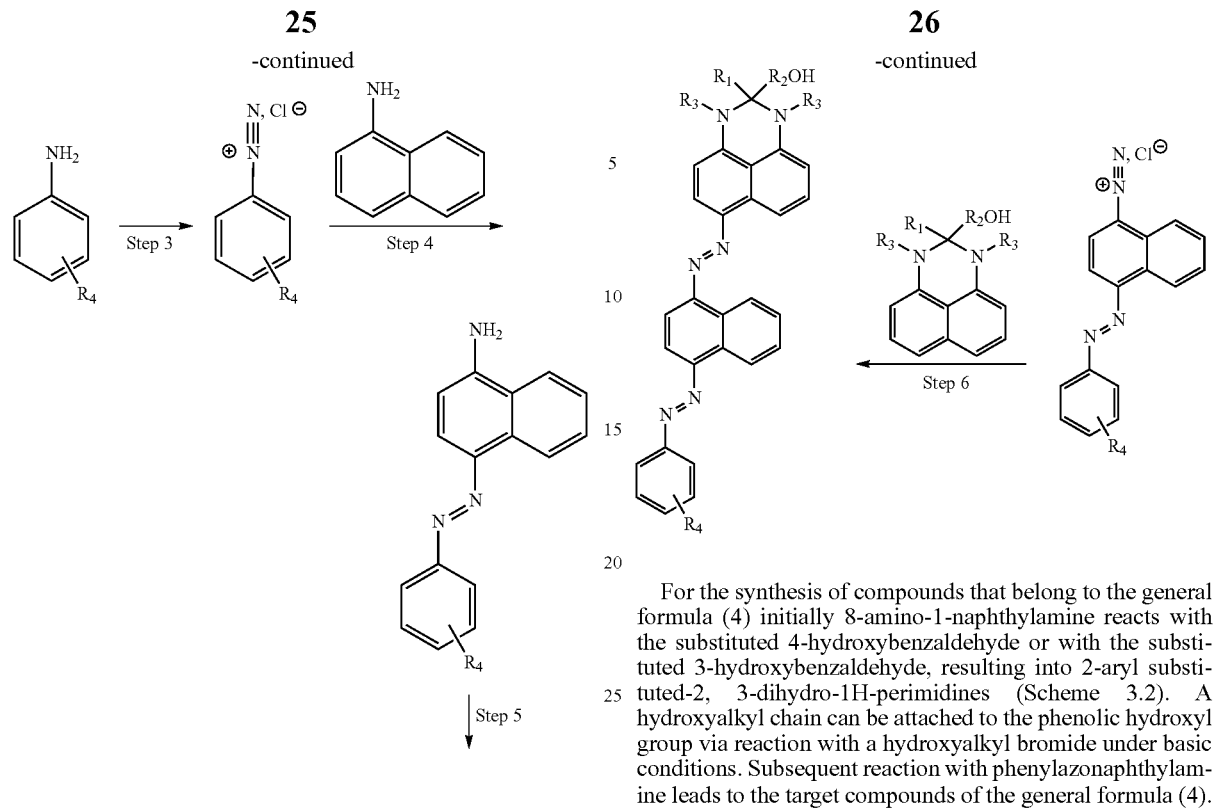

26

-continued

For the synthesis of compounds that belong to the general formula (4) initially 8-amino-1-naphthylamine reacts with the substituted 4-hydroxybenzaldehyde or with the substituted 3-hydroxybenzaldehyde, resulting into 2-aryl substituted-2, 3-dihydro-1H-perimidines (Scheme 3.2). A hydroxyalkyl chain can be attached to the phenolic hydroxyl group via reaction with a hydroxyalkyl bromide under basic conditions. Subsequent reaction with phenylazonaphthylamine leads to the target compounds of the general formula (4).

Scheme 3.2 Synthesis of compounds of the general formula (4).

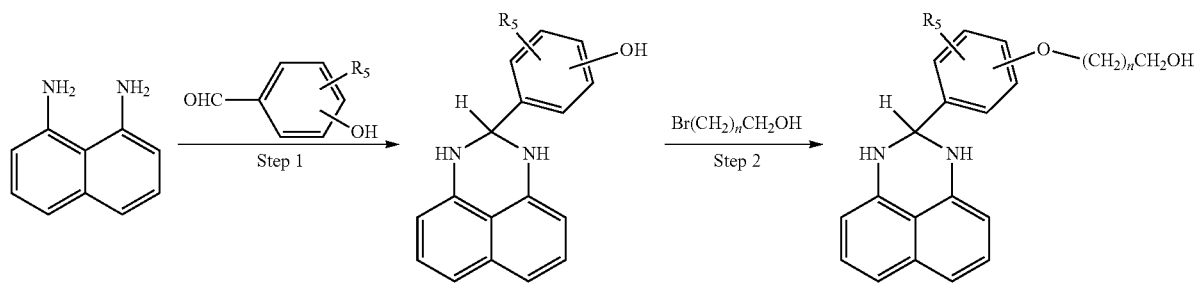

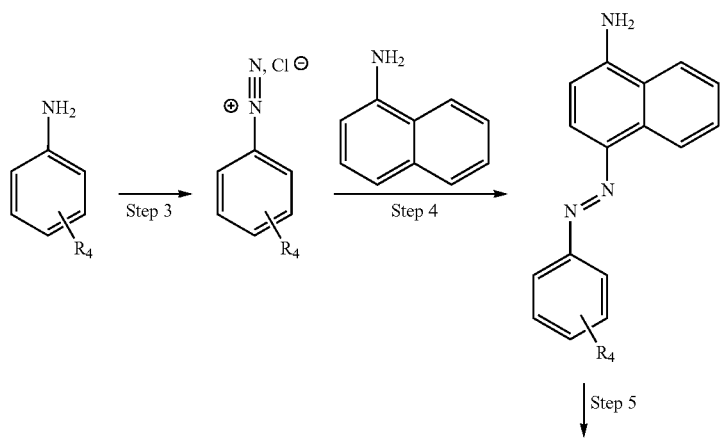

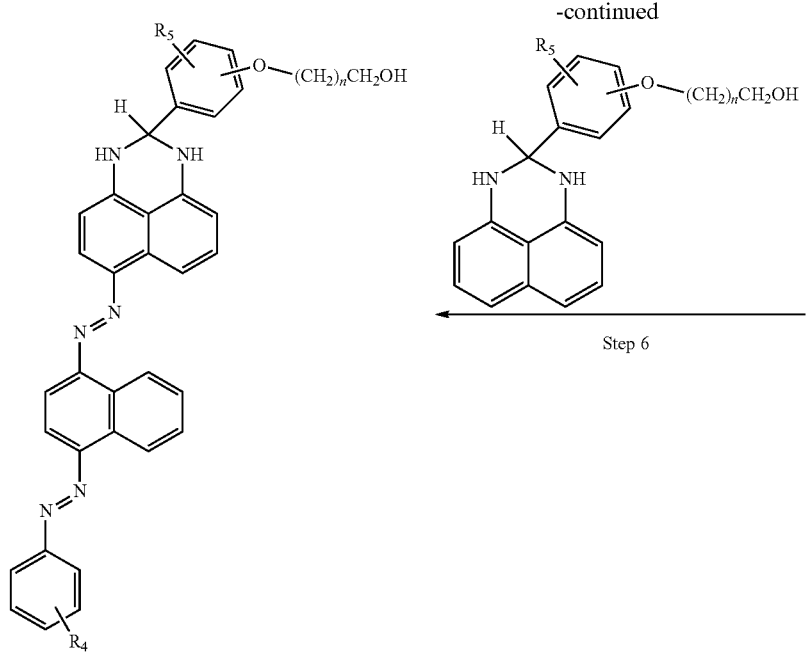
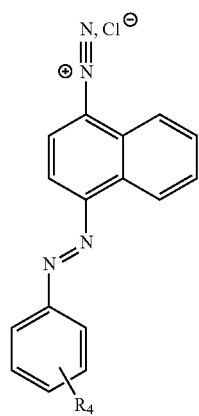

For the synthesis of compounds that belong to the general formula (5), in the first step 8-amino-1-naphthylamine reacts with the substituted ketone, and then alkyl chain can be inserted to nitrogens 1 and 3 of perimidine (Scheme 3.3). At the same time, the substituted 4-amino phenol is coupled to naphthylamine through diazotation reaction, followed by a second diazotation reaction for coupling of the former with the substituted perimidine.

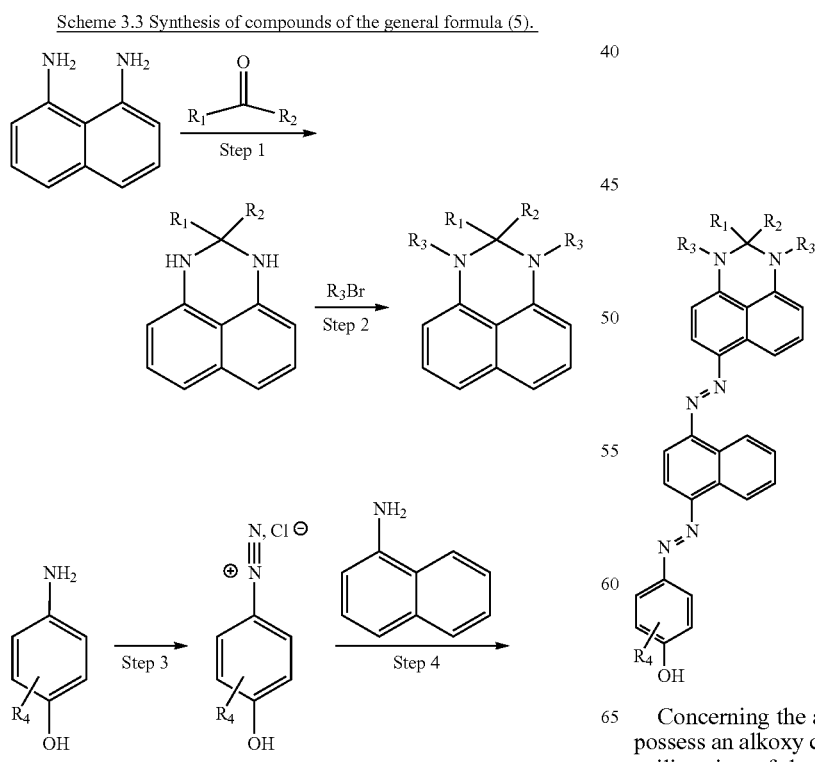

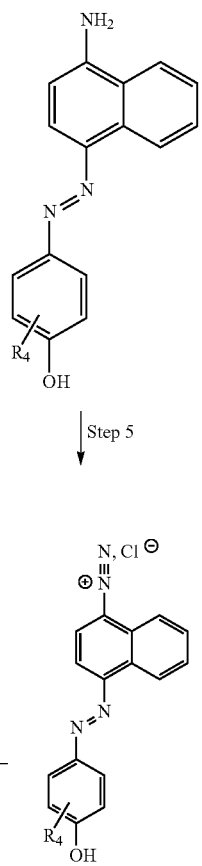

Concerning the analogues of the general formula (5) that possess an alkoxy chain between the hydroxyl group and the aniline ring of the chromophore system, these can be synthesized from the corresponding substituted 4-nitrophenols upon treatment with hydroxyalkyl bromides under basic conditions and subsequent reduction of the nitro group (Scheme 3.4).
Scheme 3.4 Synthesis of compounds of the general formula (5), that possess an alkoxy chain between the hydroxyl group and the aniline ring of the chromophore system.
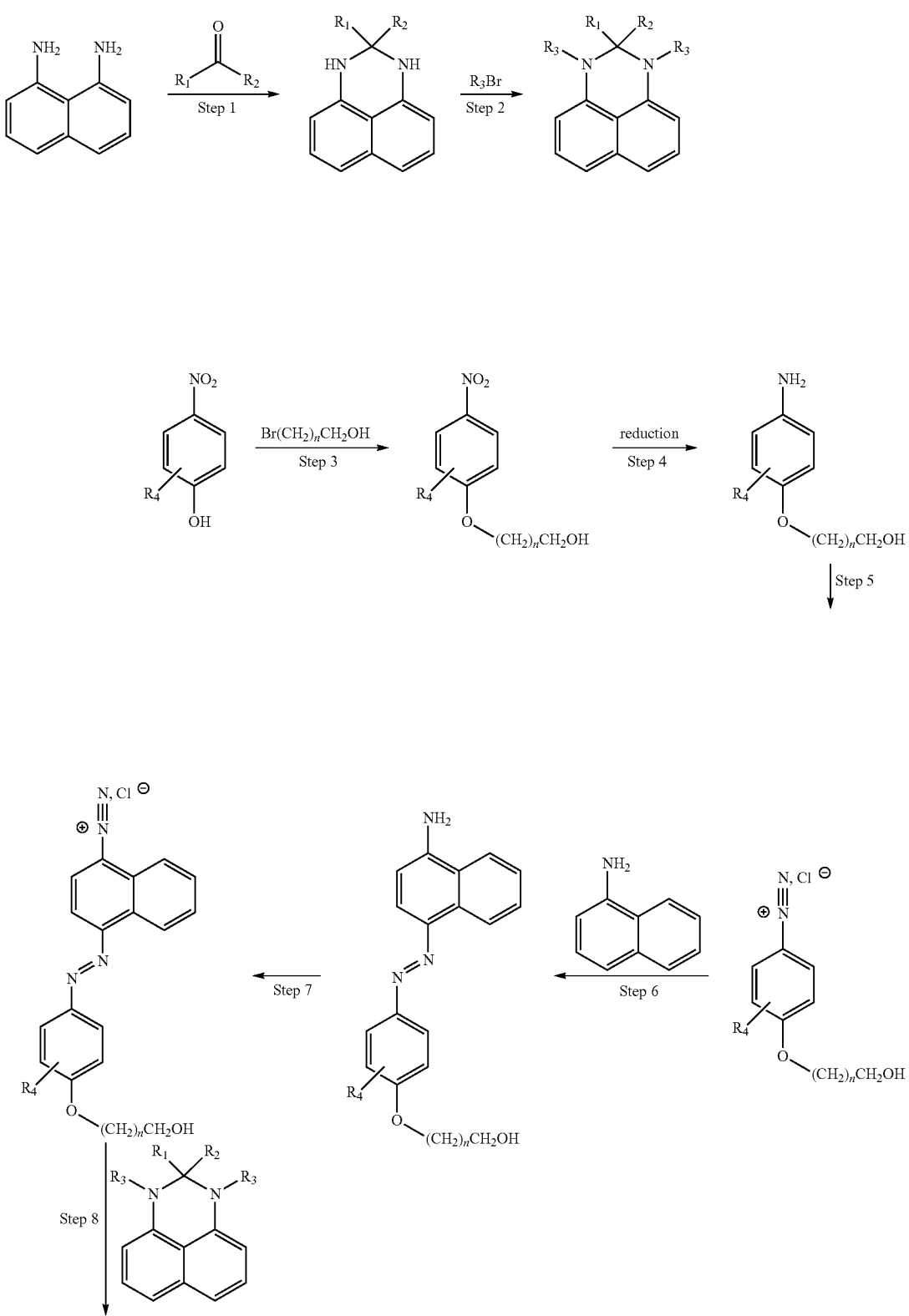

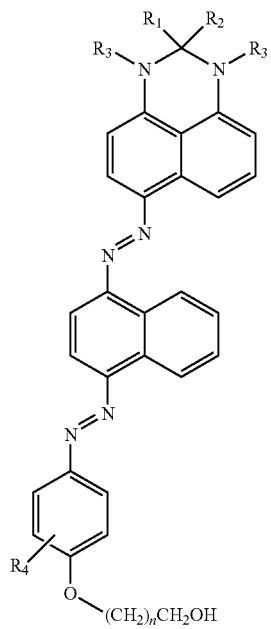

The synthesis of target compounds of the general formula (6) can be achieved by an analogous synthetic approach to the one that described above for the synthesis of compounds of general formula (5), by using the substituted 3-aminophenols as starting materials (Scheme 3.5). Concerning the analogues of the general formula (6) that possess an alkoxy chain between the hydroxyl group and the aniline ring of the chromophore system, these can be synthesized from the corresponding substituted 3-nitrophenols upon treatment with hydroxyalkyl bromides under basic conditions and subsequent reduction of the nitro group (Scheme 3.6).

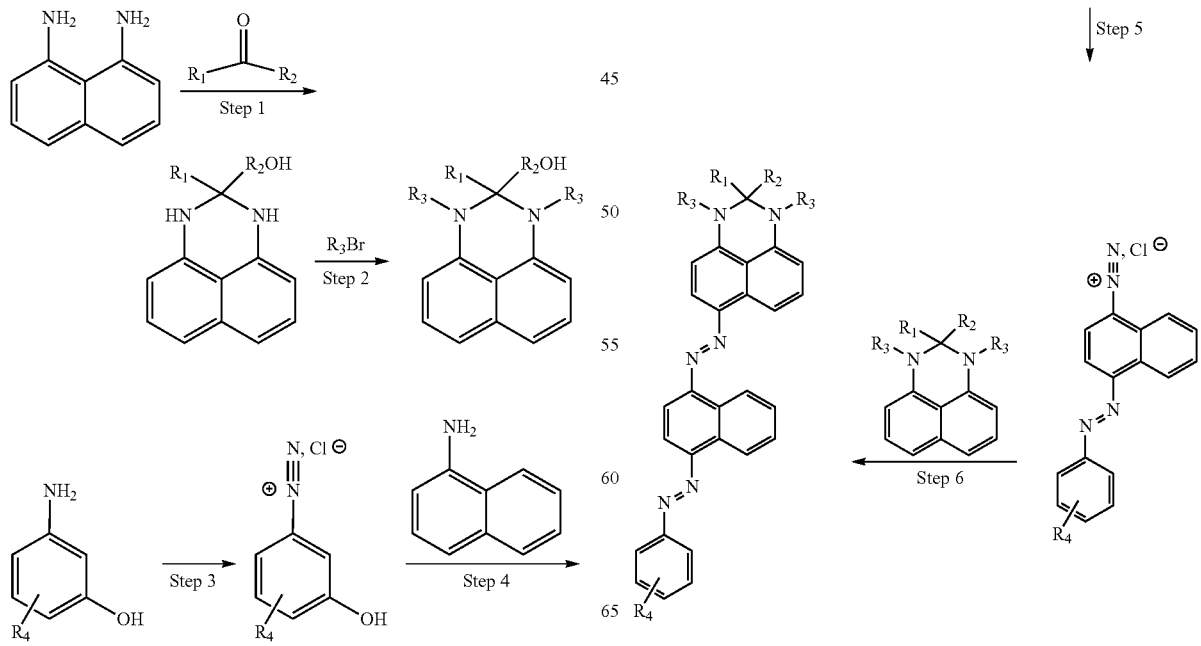

Scheme 3.5 Synthesis of compounds of the general formula (6).

Scheme 3.6 Synthesis of compounds of general formula (6), that possess an alkoxy chain between the hydroxyl group and the aniline ring of the chromophore system.
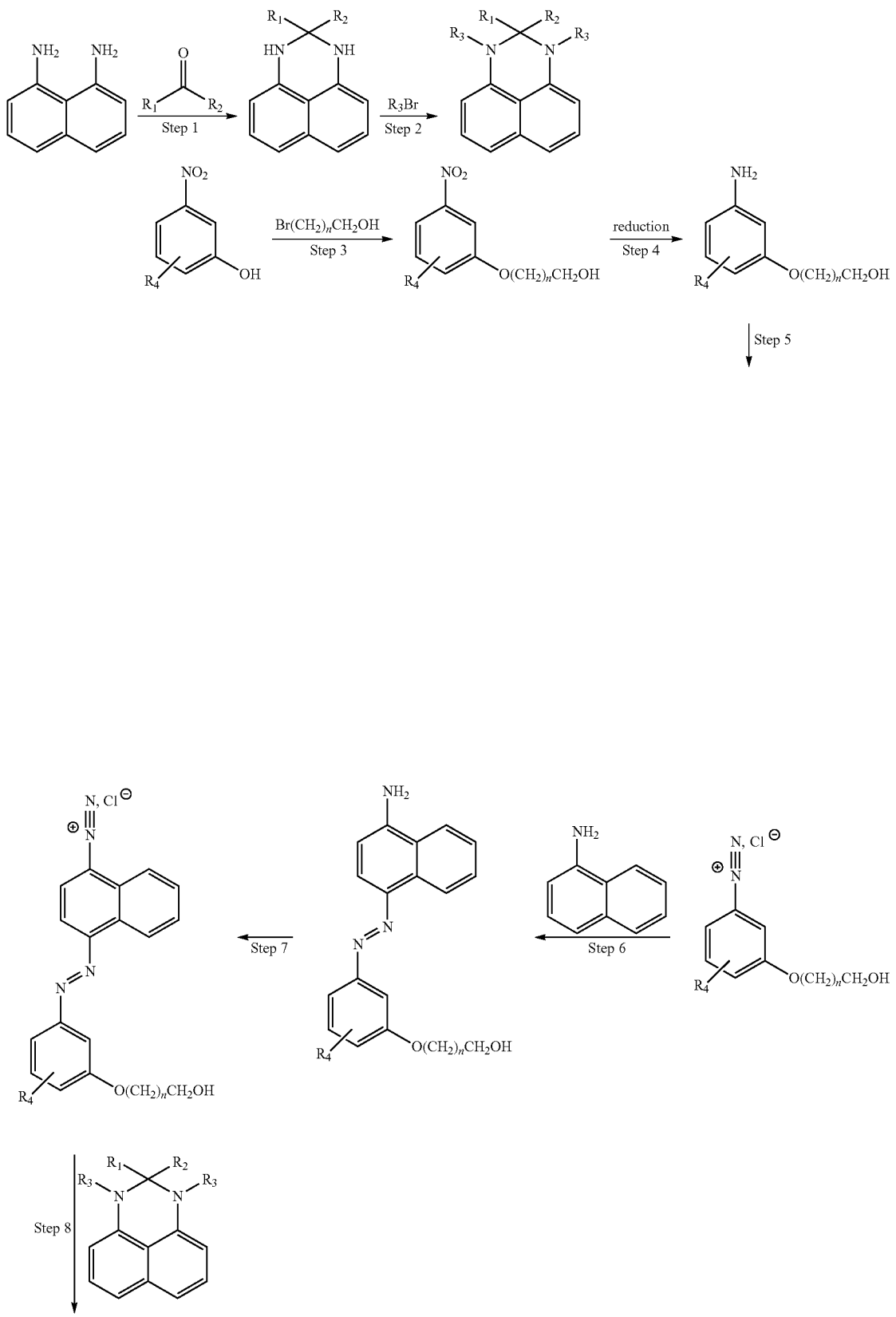

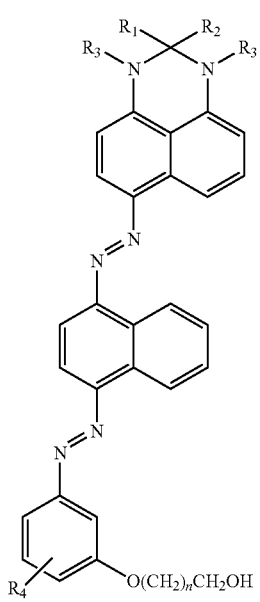

For the synthesis of target compounds that belong to the general formulas (7) and (8), the substituted para-amino phenyl alkyl alcohols or the substituted meta-amino phenyl alkyl alcohols can be used as starting materials (Schemes 3.7 and 3.8, respectively), and through the aforementioned reactions lead to the final products.

Scheme 3.7 Synthesis of compounds of the general formula (7).

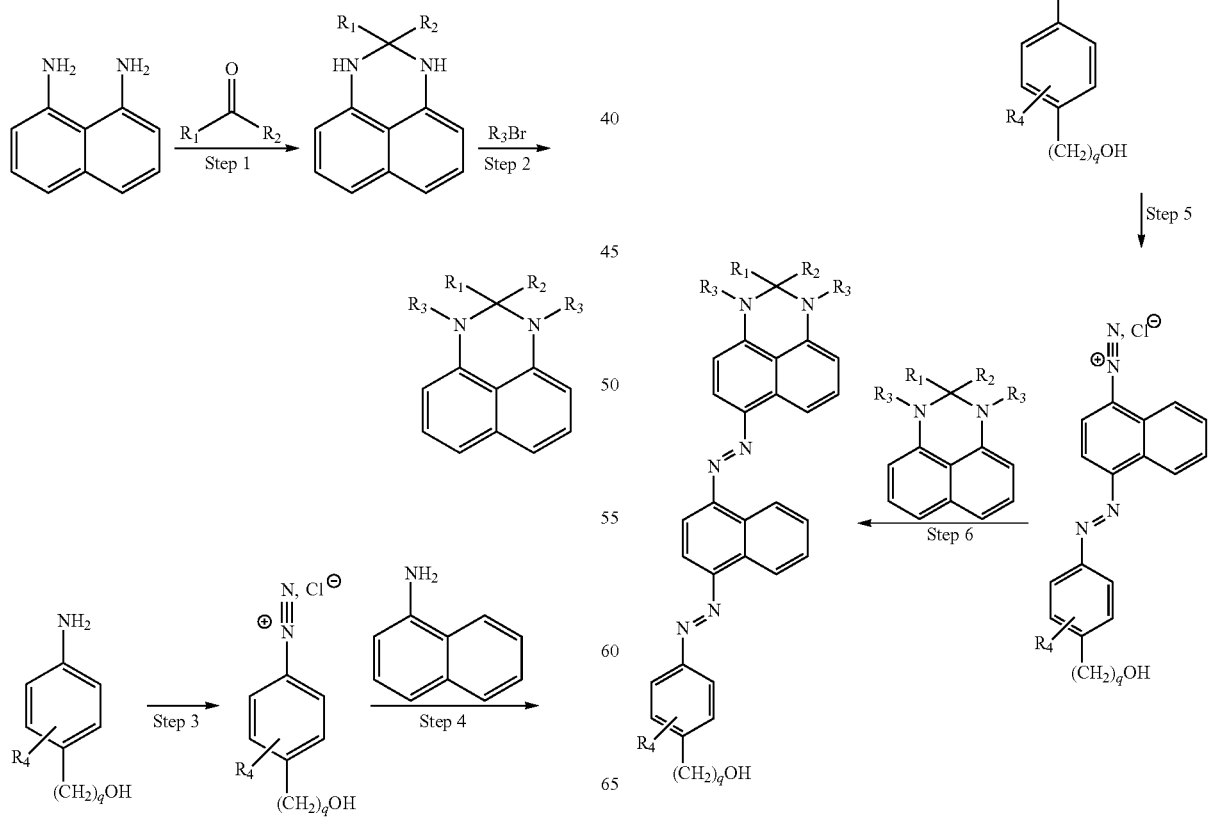

-continued

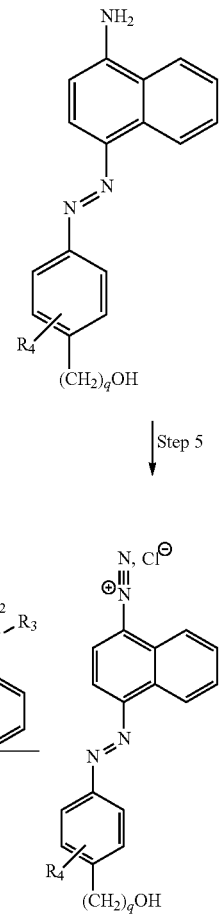

37

Scheme 3.8 Synthesis of compounds of the general formula (8).

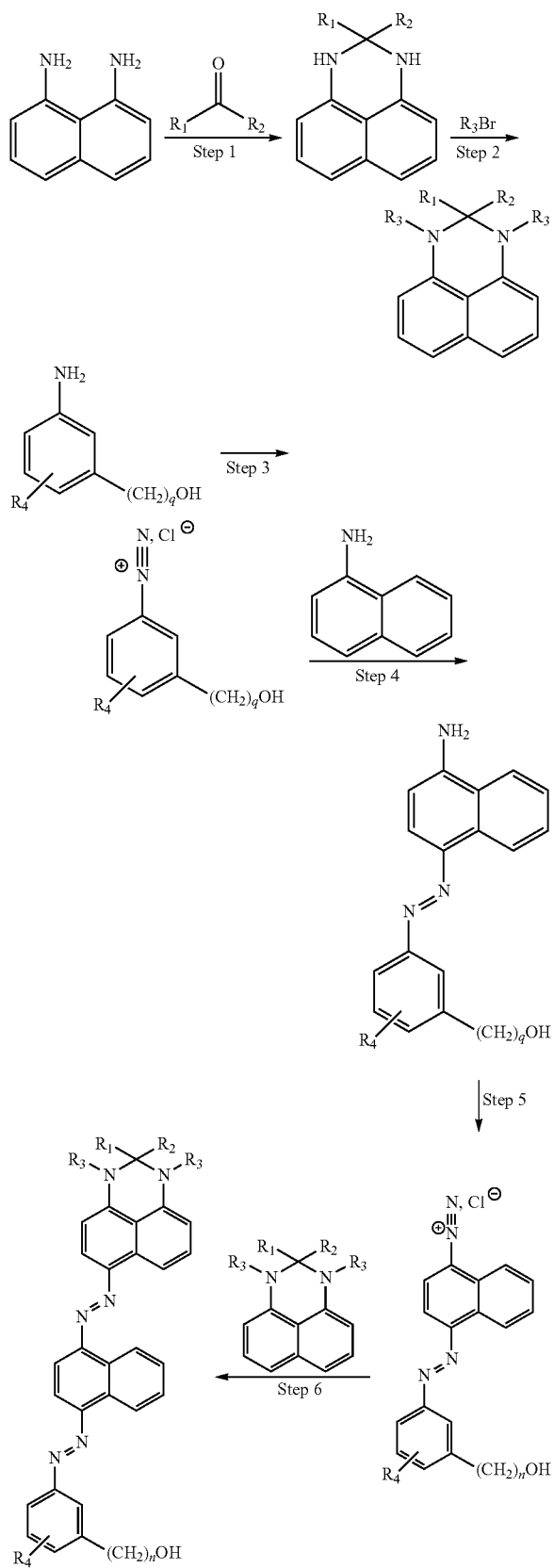

38

Uses and Applications

The present invention provides compounds that are capable of associating with lipofuscin and thus capable of application in the detection of senescent cells.

The present invention provides a use of a compound, as described hereinabove, for the detection of senescent cells.

Thus, in one aspect, the present invention provides the use of a compound of general formula (1) or (2) (or any one of compounds of sub-formulae (3) to (8)) for the detection of senescent cells.

The present invention also provides a use of a compound, as described hereinabove, for the detection of single senescent cells or senescent cells in mixed cell populations through reacting with lipofuscin in a similar manner to the Sudan Black B histochemical dye.

Moreover, the present invention also provides a use of a compound, as described hereinabove, for the detection of senescent cells in: i) tissues of animal origin, ranging from invertebrates to mammals, including humans; ii) single animal cells either derived from the above tissues or in suspension.

Furthermore, the present invention provides a use of a compound, as described hereinabove, for the detection of senescent cells in biological samples, characterized in that the biological samples are in a fresh or preserved state.

Methods and Kits

The present invention also provides a method for detecting senescence, the method comprising contacting (i.e. reacting) a compound, as defined hereinabove, with a sample of single or mixed cells, in the presence of lipofuscin.

In an embodiment, the single or mixed cells are from tissue samples of animal origin. It will be appreciated that the single or mixed cells may be from normal tissue samples of animal origin or from tissue samples of a pathologic condition of animal origin.

In an embodiment, the single or mixed cells are from tissue samples of human origin. It will again be appreciated that the single or mixed cells may be from normal tissue samples of human origin or from tissue samples of a pathologic condition of human origin.

In yet another embodiment, the single or mixed cells are from tissue samples of plant The compounds of the present invention described herein are compatible with senescent cell detection in a wide range of in vivo and in vitro biosamples. Specifically these samples can be:

1) Tissues of animal origin: senescent cells that accumulate lipofuscin can be detected in tissues (in situ) from lower (evolutionary) invertebrates up to mammals, including humans, using any of the compounds described herein.

2) Single animal cells: either derived from the above tissues using tissue disaggregation methods or that are in suspension, for example blood cells, or grown in laboratory culture can be evaluated for the senescence state by using any of the compounds described herein.

3) Plant origin: senescent cells that accumulate lipofuscin can be detected in such tissues too.

4) The biological materials described at points 1), 2) and 3) can be either in:
   i) a fresh state; or
   ii) preserved (fixed), to avoid decomposition, by physical means such as freezing, or by chemical treatment, such as immersion in formaldehyde, including if necessary, embedding in inert supportive material, like paraffin.

Notably, the vast majority of sample biobanks available in hospitals, research institutions, private clinics, etc., are in the form of fixed tissues that are usually embedded in paraffin to facilitate thin-sectioning for further analyses.

The current invention is based on the ability of these new compounds to reveal the presence of senescent cells in vivo and in vitro, upon reacting with lipofuscin, and to distinguish them from non-senescent ones.

In one embodiment of the method of this invention fresh sections, or single cells (e.g. as spreads on microscopy coverslips), or preserved (fixed) tissues sections can be histochemically stained as follows:
- a. Cell spreads should be immersed for 5-10 min in 70% ice-cold ethanol or methanol (v/v) solution.
- b. For fresh tissue sections (cryosections) 5-10 min incubation in 70% ice-cold ethanol or methanol (v/v) solution should be used instead of the above step.
- c. Fixed tissue sections should be deparaffinized for 5 min at room temperature in xylene (if sections are obtained from paraffin embedded blocks) followed by gradual rehydration of biopsy material, usually tissues, in solutions of descending concentration of ethanol (100%, 80%, 70%, 50% v/v) and finally in TBS (Tris-buffered saline) or PBS (Phosphate-buffered saline) solution.
- d. Application of SBB analogue, diluted in ethanol and filtered, on biopsy material for 10 min.
- c. Quick wash in 50% (v/v) ethanol.
- d. Transfer and wash in TBS or PBS solution.
- e. Counterstain with hematoxylin or Nuclear Fast Red, followed by mounting with glycerol and sealed with a cover slip.
- f. Microscopy observation.

These procedures allow for identification of senescent cells using these new SBB analogues in a similar histochemical fashion like the SBB, but with improved performance and bypassing ethanol solubility problems.

According to a further aspect of the present invention, there is provided a kit for detecting senescence and differentiating senescent cells comprising:
- a. a compound of general formula 1, as defined hereinabove; and
- b. one or more additional reagents required to implement a method of the present inventions, as defined hereinabove.

According to another aspect of the present invention, there is provided a kit for detecting senescence and differentiating senescent cells comprising:
- a. a lyophilized compound of general formula 1, as defined hereinabove;
- b. ethanol solution to dilute the lyophilized compound;
- c. streptavidin-HRP conjugated solution;
- d. 3,3'-diaminobenzidine; and
- e. hematoxylin or Nuclear Fast Red.

Thus, the above methods can provide the basis to develop a kit for detection of senescence for commercial exploitation. The kit has as principal component an SBB analogue. Positive and negative controls can also be included or suggested along with detailed instructions for the optimum application of the methods. The kit can find application in the following fields: biomedical research, clinical/health care, cosmetics, male and female infertility/subfertillity, animal/plant farming and the food industry. Routine detection of senescent cells can be achieved in: i) tissues of animal origin, ranging from invertebrates to mammals, including humans, ii) single animal cells either derived from the above tissues or in suspensions, body fluids and cell scrapes/smears, for example blood samples, urine specimens or cervical smears, or in laboratory culture, and iii) in tissues or cells of plant origin. Tissues or single cells can be either from healthy or pathological conditions such as aged tissues, regenerating tissues, tumors, degenerative diseases and the like. All these biological materials can be either in a fresh or preserved state (e.g. by physical or chemical means, such as freezing or formaldehyde treatment) as well as embedded in inert supportive material, like paraffin.

EXAMPLES

The following examples serve to illustrate certain preferred embodiments and aspects of the present disclosures and are not construed as limiting the scope of the invention.

Compound Synthesis

General Information:

Melting points were determined on a Büchi apparatus and are uncorrected. $^1$H-NMR spectra and $^{13}$C-NMR spectra were recorded on a Bruker Avance 600 instrument, in deuterated solvents and were referenced to TMS (δ scale). Flash chromatography was performed on Merck silica gel 60 (0.040-0.063 mm). Analytical thin layer chromatography (TLC) was carried out on precoated (0.25 mm) Merck silica gel F-254 plates. 1-Naphthylamine and 5-hydroxy-2-pentanone were purchased from Sigma-Aldrich, while the rest of the reagents were purchased from Alfa-Aesar, and all of them were used with no further purification.

Mass spec a were recorded with a LTQ Orbitrap Discovery instrument, possessing an Ionmax ionization source. Elemental analyses were undertaken using a PerkinElmer PE 240C elemental analyzer (Norwalk, Conn., U.S.) and the measured values for C, H, and N were within ±0.4% of the theoretical values.

Example 1

Synthesis of (2-methyl-6-((E)-(4-((E)-phenyldiazenyl)naphthalen-1-yl)diazenyl)-2,3-dihydro-1H-perimidin-2-yl)methanol (Scheme 3.9)

Scheme 3.9. Synthesis of (2-methyl-6-((E-(4-((E)-phenyldiazenyl)naphthalen-1-yl)diazenyl)-2,3-dihydro-1H-perimidin-2-yl)methanol.

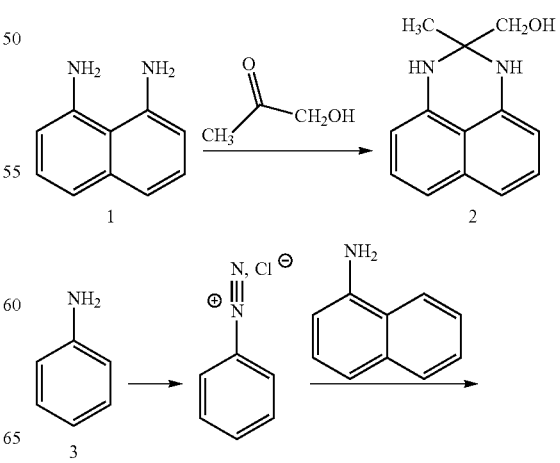

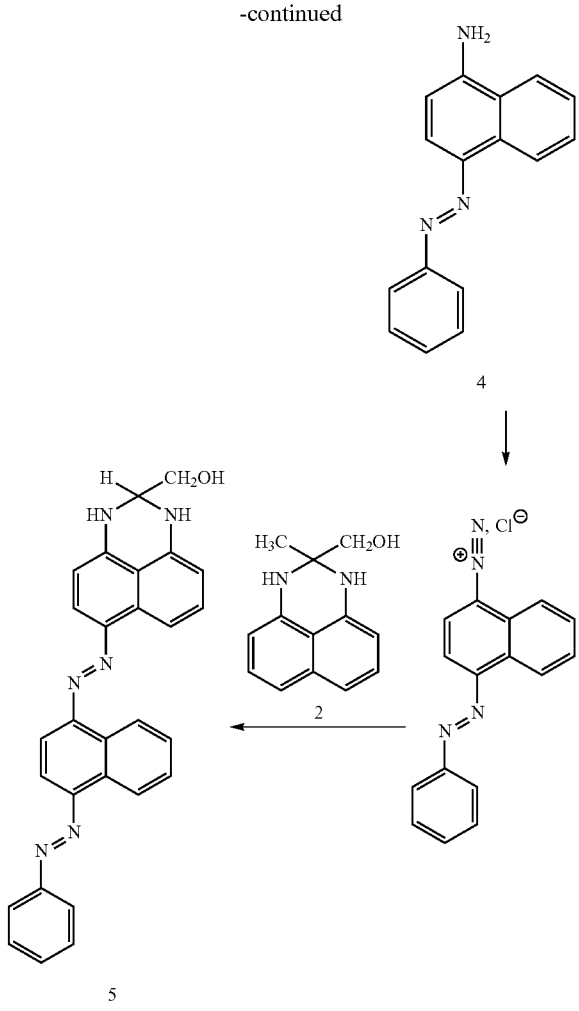

Step 1: Synthesis of (2-methyl-2,3-dihydro-1H-perimidin-2-yl)methanol (2)

1,8-Diaminonaphthalene (1, 4.3 g, 27.18 mmol) was added in a flask containing 5 ml (72.89 mmol) of hydroxyacetone and the resulting mixture was heated at 70° C. for 3 hrs. Upon completion of reaction (checked by TLC), the mixture was allowed to reach room temperature and then it was diluted with 100 ml of water, followed by extraction with $CH_2Cl_2$ (3×80 ml). Combined organic layers were washed with 200 ml of $H_2O$ and finally with 150 ml of a saturated aqueous solution of NaCl. Organic layer was dried over sodium sulfate and evaporated under reduced pressure, to provide 5.2 g of 2, as a beige solid, which was used to the next step without further purification. Yield 89%. M.p. 126-7° C. $^1$H-NMR (600 MHz, $CDCl_3$) δ 1.46 (s, 3H), 3.62 (s, 2H), 3.60-3.80 (brs, 2H, $D_2O$ exch.), 6.57 (d, 2H, J=7.2 Hz), 7.20 (d, 2H, J=7.5 Hz), 7.24 (t, 2H, J=8.2 Hz). $^{13}$C-NMR (151 MHz, $CDCl_3$) δ 24.69, 67.06, 67.13, 107.10, 113.34, 118.02, 127.18, 134.69, 139.20.

Step 2: Synthesis of (E)-4-(phenyldiazenyl)naphthalen-1-amine (4)

Aniline (3, 3.3 ml, 36.4 mmol) was added into a mixture of $H_2O$ (10 ml) and HCl (10N, 7.4 ml) at 0° C. followed by dropwise addition of an aqueous solution (6 ml) of $NaNO_2$ (2.52 g, 36.5 mmol) over a period of 5 minutes and then this mixture is left stirring at 0° C. for 2 hrs. Then sodium acetate trihydrate was added to the solution until pH was 5 and then the diazonium salt was added dropwise into a suspension of 1-naphthylamine (5.2 g, 36.32 mmol) in a mixture of $H_2O$ (100 ml), EtOH (15 ml) and HCl (10N, 3.6 ml) over a period of 30 minutes. The deep purple coloured suspension was left stirring at 0° C. for 2 hours and then an additional amount of $H_2O$ (50 ml) and EtOH (25 ml) was added and stirring was continued at room temperature for 16 hours. The solution was then neutralized with addition of saturated aqueous solution of $NaHCO_3$ and the resulting red precipitate was filtered under vacuum, washed with $H_2O$ adequately and left air dried. Crude product was purified by column chromatography using a mixture of cyclohexane/dichloromethane (from 50/50 up to 0/100, v/v) as the eluent to provide 6.4 g of 4 as a red solid. Yield 71%. M.p. 126-8° C. $^1$H-NMR (600 MHz, $CDCl_3$) δ 4.55 (brs, 2H, $D_2O$ exch.), 6.77 (d, 1H, J=7.8 Hz), 7.48 (t, 1H, J=8.2 Hz), 7.54 (m, 1H), 7.58 (t, 2H, J=7.9 Hz), 7.68 (m, 1H), 7.77 (d, 1H, J=9.3 Hz), 7.98 (d, 1H, J=7.8 Hz), 8.07 (d, 2H, J=7.2 Hz), 9.12 (d, 1H, J=10.3 Hz). $^{13}$C-NMR (151 MHz, $CDCl_3$) δ 109.15, 113.99, 120.71, 122.51, 122.73, 124.14, 125.39, 127.17, 129.13, 129.86, 133.22, 140.39, 146.39, 153.64.

Step 3: Synthesis of (2-methyl-6-((E)-(4-((E)-phenyldiazenyl)naphthalen-1-yl)diazenyl)-2,3-dihydro-1H-perimidin-2-yl)methanol (5)

(E)-4-(Phenyldiazenyl)naphthalen-1-amine (4, 0.5 g, 2.02 mmol) was dissolved in DMF (2 ml) and then $H_2O$ (3 ml) and HCl (10N, 0.6 ml) were added. This mixture was cooled at 0° C. and then an aqueous solution (1 ml) of $NaNO_2$ (139 mg, 2.02 mmol) was added dropwise over a period of 5 minutes. The diazonium salt was left stirring at 0° C. for 2 hours and then was added dropwise into a beaker containing perimidine 2 (473 mg, 2.02 mmol) in ethanol (6 ml) under vigorous stirring at 0° C. The reaction mixture was left stirring at 0° C. for 30 minutes and then at room temperature for 90 minutes. The solution was then neutralized with addition of saturated aqueous solution of $NaHCO_3$ and the resulting dark precipitate was left standing at 0° C. for 60 minutes and then filtered under vacuum, washed with $H_2O$ and left air dried. Crude product was purified by column chromatography using a mixture of dichloromethane/ethyl acetate (from 100/0 up to 100/30, v/v) as the eluent to provide 0.45 g of 5 as a black solid. Yield 47%. M.p.>270° C.$_{(decomp.)}$. $^1$H-NMR (600 MHz, $CDCl_3$) δ 1.57 (s, 3H), 3.66 (s, 2H), 4.55 (brs, 1H, $D_2O$ exch.), 5.02 (brs, 1H, $D_2O$ exch.), 6.60 (d, 1H, J=8.2 Hz), 6.65 (d, 1H, J=7.2 Hz), 7.47 (t, 1H, J=7.9 Hz), 7.51 (t, 1H, J=7.3 Hz), 7.57 (t, 2H, J=7.5 Hz), 7.72 (m, 2H), 7.97 (d, 1H, J=8.2 Hz), 8.01 (m, 1H), 8.08 (d, 2H, J=7.6 Hz), 8.14 (m, 1H), 8.45 (m, 1H), 9.03 (m, 1H), 9.11 (m, 1H). $^{13}$C-NMR (151 MHz, $CDCl_3$) δ 24.84, 67.27, 67.40, 106.31, 107.64, 112.29, 112.76, 113.72, 116.95, 123.43, 123.67, 124.19, 126.88, 127.21, 129.32, 131.19, 132.65, 133.81, 139.63, 140.94, 144.47, 147.96, 150.48, 153.61.

Example 2

Synthesis of 4-(6-((E)-(4-((E)-phenyldiazenyl)naphthalen-1-yl)diazenyl)-2,3-dihydro-1H-perimidin-2-yl)phenol (Scheme 3.10)

Scheme 3.10. Synthesis of 4-(6-((E-(4-((E)-phenyldiazenyl)naphthalen-1-yl)diazenyl)-2,3-dihydro-1H-perimidin-2-yl)phenol.

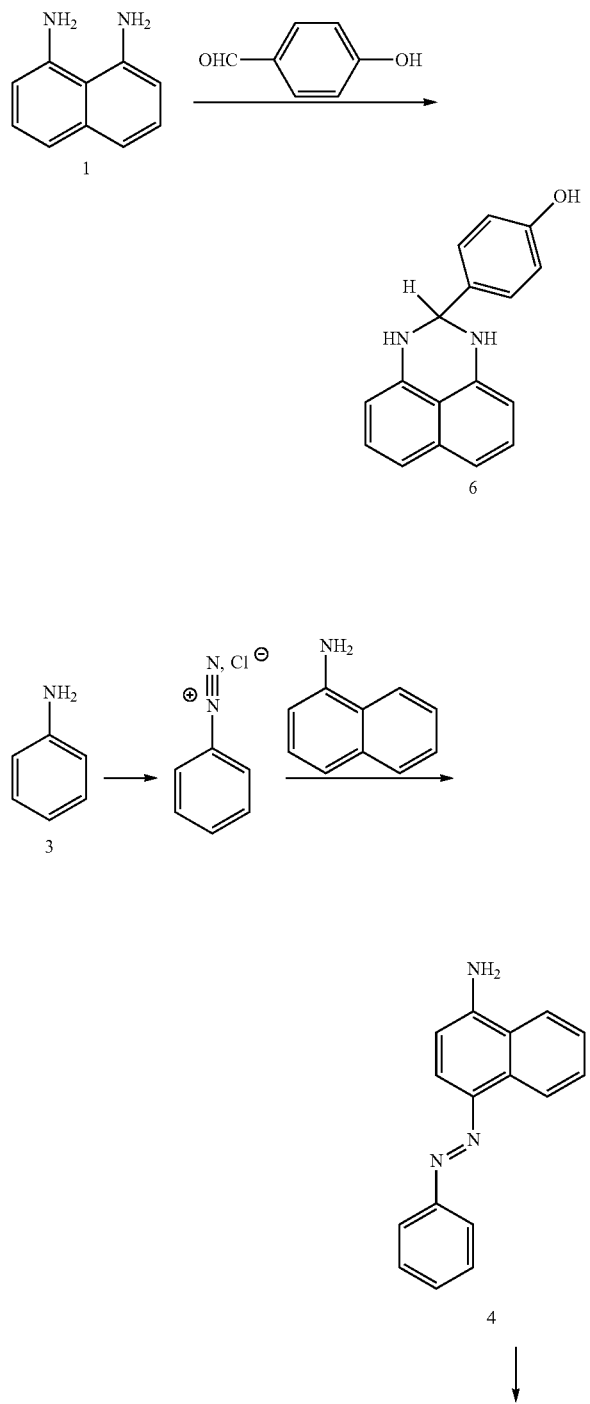

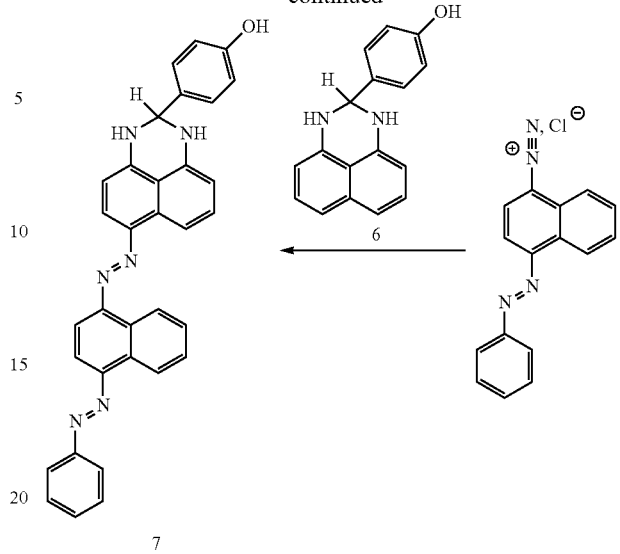

Step 1: Synthesis of 4-(2,3-dihydro-1H-perimidin-2-yl)phenol (6)

4-Hydroxybenzaldehyde (2.32 g, 18.96 mmol) was added into a solution of 1,8-diaminonaphthalene (1, 3 g, 18.96 mmol) in ethanol (15 mL) and this mixture was refluxed for 40 minutes. Upon completion of reaction, the mixture was allowed to reach room temperature and the solid that precipitated was filtered under vacuum, washed with ethanol (10 mL) and left air-dried. Finally, 4.95 g of compound 6 were obtained as an off-white solid. Yield 100%. M.p. 169-171° C. $^{1}$H-NMR (600 MHz, DMSO-d6) δ 5.25 (s, 1H), 6.48 (d, 2H, J=7.4 Hz), 6.58 (brs, 2H, D$_2$O exch.), 6.81 (d, 2H, J=8.5 Hz), 6.97 (d, 2H, J=8.1 Hz), 7.14 (t, 2H, J=7.7 Hz), 7.41 (d, 2H, J=8.5 Hz), 9.48 (brs, 1H, D$_2$O exch.). $^{13}$C-NMR (151 MHz, DMSO-d6) δ 66.32, 104.22, 112.48, 114.86, 115.13, 126.80, 129.13, 131.96, 134.42, 143.44, 157.73.

Step 2: Synthesis of 4-(6-((E)-(4-((E)-phenyldiazenyl)naphthalen-1-yl)diazenyl)-2,3-dihydro-1H-perimidin-2-yl)phenol (7)

(E)-4-(Phenyldiazenyl)naphthalen-1-amine (4, 0.5 g, 2.02 mmol, its synthesis is described at step 2 of the typical example 1) was dissolved in DMF (2 ml) and then H$_2$O (6 ml) and HCl (10N, 0.6 ml) were added. This mixture was cooled at 0° C. and then an aqueous solution (1 ml) of NaNO$_2$ (139 mg, 2.02 mmol) was added dropwise over a period of 5 minutes. The diazonium salt was left stirring at 0° C. for 2 hours and then it was added dropwise into a beaker containing perimidine 6 (529 mg, 2.02 mmol) in ethanol (10 ml) under vigorous stirring at 0° C. The reaction mixture was left stirring at 0° C. for 30 minutes and then at room temperature for 90 minutes. The solution was then neutralized with addition of saturated aqueous solution of NaHCO$_3$ and the resulting dark precipitate was left standing at 0° C. for 60 minutes and then filtered under vacuum, washed with H$_2$O and left air dried. Crude product was purified by column chromatography using a mixture of dichloromethane/ethyl acetate (from 100/0 up to 100/4, v/v) as the eluent to provide 0.62 g of 7 as a black solid. Yield 59%. M.p.>270° C.$_{(decomp.)}$. $^1$H-NMR (600 MHz, DMSO-d6) δ 5.59 (s, 1H), 6.68 (d, 1H, J=6.9 Hz), 6.72 (d, 1H, J=8.5 Hz), 6.87 (d, 2H, J=8.5 Hz), 7.07 (brs, 1H, D$_2$O exch.), 7.43-7.49 (m, 3H), 7.59 (t, 1H, J=7.4 Hz), 7.65 (t, 2H, J=7.6 Hz), 7.77-7.84 (m, 2H), 7.99 (d, 1H, J=8.4 Hz), 8.04 (d, 1H, J=8.4 Hz), 8.08 (d, 2H, J=7.5 Hz), 8.17-8.21 (m, 2H), 8.24 (d, 1H, J=8.4 Hz), 9.01 (m, 1H), 9.10 (m, 1H), 9.61 (brs, 1H, D$_2$O exch.). $^{13}$C-NMR (151 MHz, DMSO-d6) δ 65.89, 105.23, 105.76, 110.51, 110.82, 111.34, 112.78, 115.09, 118.74, 122.93, 123.04, 123.83, 126.98, 127.61, 129.04, 129.55, 130.07, 131.05, 131.21, 131.46, 132.02, 133.55, 138.64, 143.63, 145.95, 149.10, 150.06, 152.85, 158.05.

Example 3

Synthesis of 3-((E)-(4-((E)-(2,2-dimethyl-2,3-dihydro-1H-perimidin-6-yl)diazenyl)naphthalen-1-yl)diazenyl)phenol (Scheme 3.11)

Step 1: Synthesis of 2,2-dimethyl-2,3-dihydro-1H-perimidine (8)

1,8-Diaminonaphthalene (1, 4 g, 25.28 mmol) was added into a flask containing 14 mL of acetone and this reaction mixture was left stirring at room temperature for 60 hours. Upon completion of reaction the solvent was evaporated under reduced pressure, diethylether (40 mL) was added into the oily residue and evaporated, causing the crystallization of the perimidine 8. By this procedure 5 g of the perimidine 8 were obtained, as a beige solid. Yield 100%. M.p. 114-116° C. $^1$H-NMR (600 MHz, CDCl$_3$) δ 1.46 (s, 6H), 4.14 (brs, 2H, D$_2$O exch.), 6.48 (d, 2H, J=7.3 Hz), 7.19 (d, 2H, J=7.9 Hz), 7.27 (t, 2H, J=7.4 Hz+8.1 Hz). $^{13}$C-NMR (151 MHz, CDCl$_3$) δ 28.80, 64.62, 106.06, 113.05, 117.14, 127.12, 134.70, 140.34.

Scheme 3.11. Synthesis of 3-((E-(4-((E)-(2,2-dimethyl-2,3-dihydro-1H-perimidin-6-yl)diazenyl)naphthalen-1-yl)diazenyl)phenol.

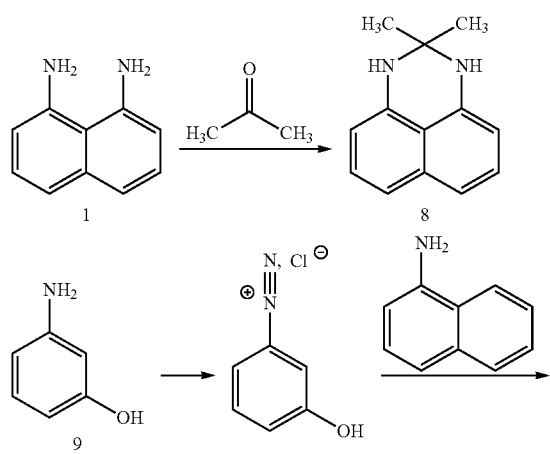

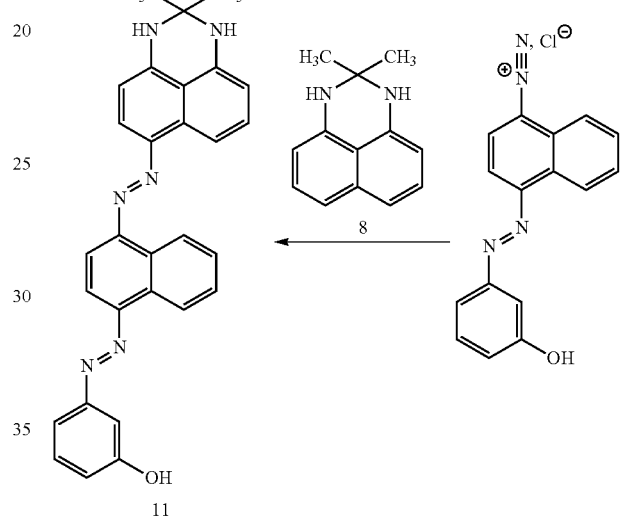

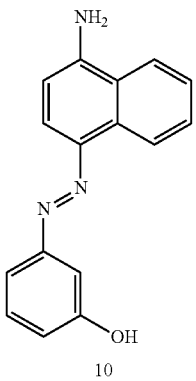

10

Step 2: Synthesis of (E)-3-((4-aminonaphthalen-1-yl)diazenyl)phenol (10)

3-Aminophenol (9, 2 g, 18.2 mmol) was added into a mixture of H$_2$O (5 ml) and HCl (10N, 3.5 ml) at 0° C. followed by dropwise addition of an aqueous solution (3 ml) of NaNO$_2$ (1.26 g, 18.25 mmol) over a period of 5 minutes and then this mixture is left stirring at 0° C. for 2 hrs. Then 100 mg of amidosulfonic acid was added to the solution and stirring was continued for 15 more minutes. This solution of the diazonium salt was added dropwise into a suspension of 1-naphthylamine (2.6 g, 18.16 mmol) in a mixture of H$_2$O (50 ml), EtOH (6 ml) and HCl (10N, 2 ml) over a period of 30 minutes. The deep purple colored suspension was left stirring at 0° C. for 90 minutes and then at room temperature for 16 hours. The solution was then neutralized with addition of saturated aqueous solution of NaHCO$_3$ and the resulting precipitate was filtered under vacuum, washed with H$_2$O adequately and left air dried. Crude product was purified by column chromatography using a mixture of dichloromethane/ethyl acetate (from 100/0 up to 100/10, v/v) as the eluent to provide 2.8 g of 10 as an orange colored solid. Yield 58%. M.p. 205-7° C. $^1$H-NMR (600 MHz, DMSO-d6) δ 6.79 (d, 1H, J=8.5 Hz), 6.86 (m, 1H), 6.91 (brs, 2H, D$_2$O exch.), 7.32-7.38 (m, 3H), 7.50 (t, 1H, J=7.0 Hz), 7.64 (t, 1H, J=8.0 Hz+7.2 Hz), 7.90 (d, 1H, J=8.5 Hz), 8.22 (d, 1H, J=8.5 Hz), 8.89 (d, 1H, J=8.4 Hz), 9.67 (s, 1H, D$_2$O exch.). $^{13}$C-NMR (151 MHz, DMSO-d6) δ 106.91, 107.38, 114.69, 114.94, 116.51, 121.22, 122.61, 122.67, 124.33, 127.36, 129.90, 133.24, 136.71, 150.19, 154.52, 158.15.

Step 3: Synthesis of 3-((E)-(4-((E)-(2,2-dimethyl-2,3-dihydro-1H-perimidin-6-yl)diazenyl)naphthalen-1-yl)diazenyl)phenol (11)

(E)-3-((4-Aminonaphthalen-1-yl)diazenyl)phenol (10, 526 mg, 2 mmol) was added into a mixture of H$_2$O (6 ml) and HCl (10N, 0.6 ml) at 0° C. followed by dropwise addition of an aqueous solution (1 ml) of NaNO$_2$ (138 mg, 2 mmol) over a period of 5 minutes and then this mixture is left stirring at 0° C. for 2 hrs. Then sodium acetate trihydrate (80 mg) was added to the solution and stirring was continued for 15 more minutes. This solution of the diazonium salt was added dropwise into a solution of perimidine 8 (396 mg, 2 mmol) in EtOH (10 ml) over a period of 10 minutes. The deep purple colored suspension was left stirring at 0° C. for 30 minutes and then at room temperature for 90 minutes. The solution was then neutralized with addition of saturated aqueous solution of NaHCO$_3$ and the resulting precipitate was filtered under vacuum, washed with H$_2$O adequately and left air dried. Crude product was purified by column chromatography using a mixture of cyclohexane/ethyl acetate (from 80/20 up to 60/40, v/v) as the eluent to provide 450 mg of 11 as a black solid. Yield 48%. M.p. 155-8° C.$_{(decomp.)}$. $^1$H-NMR (600 MHz, acetone-d6) δ 1.58 (s, 6H), 5.99 (brs, 1H, D$_2$O exch.), 6.62 (d, 1H, J=7.4 Hz), 6.65 (d, 1H, J=8.4 Hz), 6.99 (brs, 1H, D$_2$O exch.), 7.08 (m, 1H), 7.44 (t, 1H, J=8.2 Hz+7.6 Hz), 7.48 (t, 1H, J=7.9 Hz), 7.60 (m, 1H), 7.64 (m, 1H), 7.75-7.80 (m, 2H), 8.04 (d, 1H, J=8.3 Hz), 8.10 (d, 1H, J=8.3 Hz), 8.24 (d, 1H, J=8.5 Hz), 8.34 (d, 1H, J=8.4 Hz), 8.84 (brs, 1H, D$_2$O exch.), 9.06 (m, 1H), 9.17 (m, 1H). $^{13}$C-NMR (151 MHz, acetone-d6) δ 28.83, 66.00, 106.19, 106.89, 108.88, 111.97, 112.09, 112.44, 113.49, 117.27, 118.99, 119.46, 124.12, 124.97, 127.63, 128.16, 130.74, 131.08, 132.75, 133.58, 135.08, 140.38, 143.02, 147.67, 148.38, 151.55, 155.79, 159.31.

Example 4

Synthesis of 2-(4-((E)-(4-((E)-(2,2-dimethyl-2,3-dihydro-1H-perimidin-6-yl)diazenyl)naphthalen-1-yl)diazenyl)phenyl)ethanol (Scheme 3.12)

Step 1: Synthesis of (E)-2-(4-((4-aminonaphthalen-1-yl)diazenyl)phenyl)ethanol (13)

2-(4-Aminophenyl)ethanol (12, 4 g, 29.16 mmol) was added into a mixture of H$_2$O (12 ml) and HCl (10N, 6.4 ml) at 0° C. followed by dropwise addition of an aqueous solution (6 ml) of NaNO$_2$ (2.21 g, 32.03 mmol) over a period of 10 minutes and then this mixture is left stirring at 0° C. for 100 minutes. Then 600 mg of sodium acetate trihydrate were added to the solution and stirring was continued for 15 more minutes. This solution of the diazonium salt was added dropwise into a suspension of 1-naphthylamine (4.15 g, 29 mmol) in a mixture of H$_2$O (80 ml), EtOH (9 ml) and HCl (10N, 3 ml) over a period of 30 minutes. The deep purple colored suspension was left stirring at 0° C. for 90 minutes and then at room temperature for 16 hours. The solution was then neutralized with addition of saturated aqueous solution of NaHCO$_3$ and the resulting precipitate was filtered under vacuum, washed with H$_2$O adequately and left air dried. Crude product was purified by column chromatography using a mixture of dichloromethane/ethyl acetate (from 100/5 up to 100/25, v/v) as the eluent to provide 5.2 g of 13 as an orange colored solid. Yield 62%. M.p. 110-2° C. $^1$H-NMR (600 MHz, DMSO-d6) δ 2.81 (t, 2H, J=6.9 Hz), 3.67 (q, 2H, J=6.9 Hz+5.5 Hz), 4.69 (t, 1H, D$_2$O exch., J=5.3 Hz), 6.77 (d, 1H, J=8.5 Hz), 6.85 (brs, 2H, D$_2$O exch.), 7.38 (d, 2H, J=8.1 Hz), 7.48 (t, 1H, J=7.8 Hz+7.3 Hz), 7.62 (t, 1H, J=7.9 Hz+7.3 Hz), 7.80 (d, 2H, J=8.1 Hz), 7.88 (d, 1H, J=8.5 Hz), 8.20 (d, 1H, J=8.5 Hz), 8.90 (d, 1H, J=8.5 Hz). $^{13}$C-NMR (151 MHz, DMSO-d6) δ 38.82, 62.01, 107.31, 114.78, 121.23, 121.76, 122.61, 122.72, 124.28, 127.29, 129.72, 133.14, 136.84, 141.16, 149.96, 151.60.

Step 2: Synthesis of 2-(4-((E)-(4-((E)-(2,2-dimethyl-2,3-dihydro-1H-perimidin-6-yl)diazenyl)naphthalen-1-yl)diazenyl)phenyl)ethanol (14)

(E)-2-(4-((4-aminonaphthalen-1-yl)diazenyl)phenyl) ethanol (13, 873 mg, 3 mmol) was added into a mixture of H$_2$O (9 mL), HCl (10N, 0.9 mL) and N,N-dimethylformamide (0.6 mL) at 0° C. followed by dropwise addition of an aqueous solution (2 ml) of NaNO$_2$ (207 mg, 3 mmol) over a period of 10 minutes and then this mixture is left stirring at 0° C. for 2 hrs. Then sodium acetate trihydrate (180 mg) was added to the solution and stirring was continued for 15 more minutes. This solution of the diazonium salt was added dropwise into a solution of 2,2-dimethyl-2,3-dihydro-1H-perimidine (8, 594 mg, 3 mmol, its synthesis is described at step 1 of the typical example 3) in EtOH (10 ml) over a period of 10 minutes. The deep purple colored suspension was left stirring at 0° C. for 30 minutes and then at room temperature for 90 minutes. The solution was then neutralized with addition of saturated aqueous solution of NaHCO$_3$ and the resulting precipitate was filtered under vacuum, washed with H$_2$O adequately and left air dried. Crude product was purified by column chromatography using a mixture of dichloromethane/ethyl acetate (from 100/1 up to 100/10, v/v) as the eluent to provide 1 g of 14 as a black solid. Yield 67%. M.p. 249-252° C.$_{(decomp.)}$. $^1$H-NMR (600 MHz, DMSO-d6) δ 1.48 (s, 6H), 2.86 (t, 2H, J=6.9 Hz), 3.71 (q, 2H, J=6.9 Hz+5.1 Hz), 4.74 (t, 1H, D$_2$O exch., J=5.1 Hz), 6.56 (d, 1H, J=6.9 Hz), 6.60 (d, 1H, J=8.6 Hz), 6.78 (brs, 1H, D$_2$O exch.), 7.43 (t, 1H, J=8.1 Hz+7.7 Hz), 7.48 (d, 2H, J=8.4 Hz), 7.76-7.83 (m, 2H), 7.96-8.02 (m, 5H), 8.17 (d, 1H, J=8.9 Hz), 8.20 (d, 1H, J=8.6 Hz), 9.00 (m, 1H), 9.09 (m, 1H). $^{13}$C-NMR (151 MHz, DMSO-d6) δ 28.27, 38.90, 61.82, 64.59, 105.08, 105.53, 109.82, 109.96, 111.22, 112.64, 119.12, 122.78, 123.02, 123.77, 126.83, 127.45, 130.01, 130.28, 131.00, 131.95, 133.51, 138.25, 142.28, 143.83, 145.84, 147.82, 149.96, 151.38.

Scheme 3.12. Synthesis of 2-(4-((E-(4-((E)-(2,2-dimethyl-2,3-dihydro-1H-perimidin-6-yl)diazenyl)naphthalen-1-yl)diazenyl)ethanol.

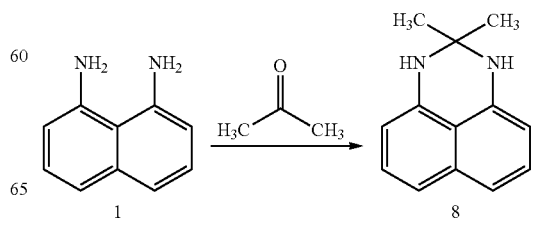

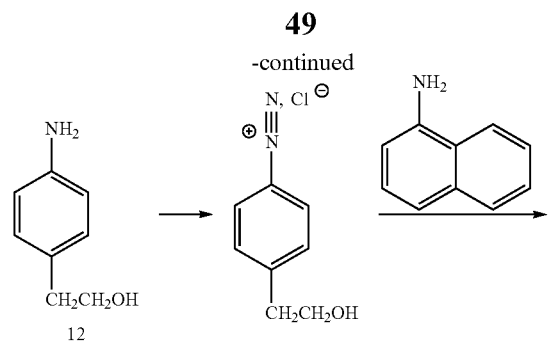
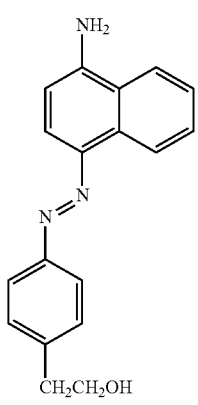
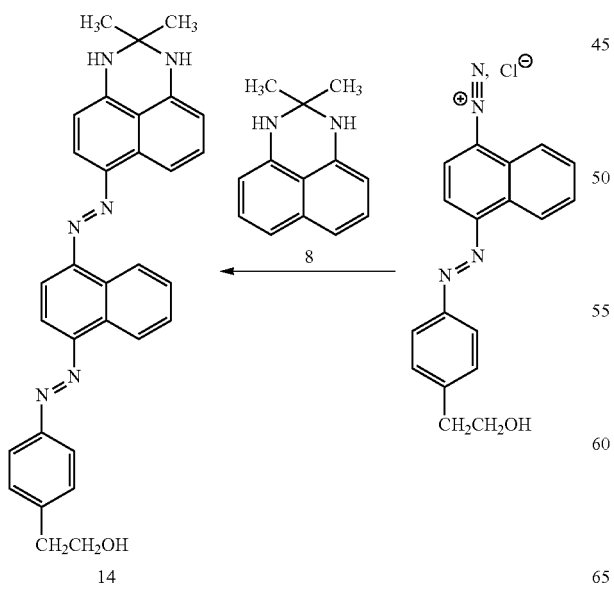

Example 5

Synthesis of Synthesis of 3-(2-Methyl-6-((E)-(4-((E)-phenyldiazenyl)naphthalen-1-yl)diazenyl)-2,3-dihydro-1H-perimidin-2-yl)propan-1-ol (16)

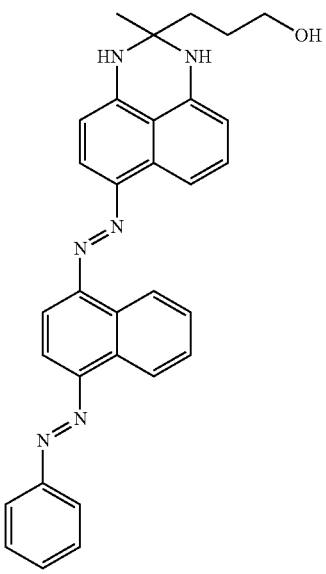

Compound 16 (3-(2-Methyl-6-((E)-(4-((E)-phenyldiazenyl)naphthalen-1-yl)diazenyl)-2,3-dihydro-1H-perimidin-2-yl)propan-1-ol) was prepared according to the general procedure described in respect of Example 1 above.

Step 1: Synthesis of 3-(2-Methyl-2,3-dihydro-1H-perimidin-2-yl)propan-1-ol (17)

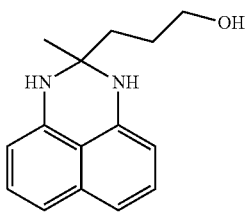

This compound was synthesized according to the general procedure described in respect of Step 1 of Example 1 above, upon reaction of 1,8-diaminonaphthalene with 5-hydroxy-2-pentanone, in 97% yield. Grey solid. M.p. 149-150° C. $^1$H NMR (600 MHz, acetone-d6) δ 1.43 (s, 3H), 1.68-1.74 (m, 2H), 1.79-1.83 (m, 2H), 3.45-3.53 (m, 3H), 5.61 (brs, 2H, D$_2$O exch.), 6.43 (d, 2H, J=7.4 Hz), 6.95 (d, 2H, J=8.1 Hz), 7.12 (t, 2H, J=7.9 Hz). $^{13}$C NMR (151 MHz, acetone-d$_6$) δ 27.20, 28.28, 38.32, 62.90, 67.07, 105.35, 113.48, 116.06, 127.93, 135.82, 142.71.

Step 2: Synthesis of (E)-4-(phenyldiazenyl)naphthalen-1-amine (4)

This compound was synthesized according to the general procedure described in respect of Step 2 of Example 1 above.

Step 3: Synthesis of 3-(2-Methyl-6-((E)-(4-((E)-phenyldiazenyl)naphthalen-1-yl)diazenyl)-2,3-dihydro-1H-perimidin-2-yl)propan-1-ol (16)

This compound was prepared according to the general procedure described in respect of Step 3 of Example 1 above, upon reaction of 4 with perimidine 17. The crude product was purified by column chromatography using a mixture of cyclohexane/ethyl acetate (from 1/1 up to 2/8, v/v) as the eluent to provide pure 16 as a black solid, in 50% yield. Mp 124-6° C. $^1$H NMR (600 MHz, acetone-$d_6$) δ 1.56 (s, 3H), 1.74-1.80 (m, 2H), 1.92-1.97 (m, 2H), 3.53-3.59 (m, 3H), 6.03 (brs, 1H, $D_2O$ exch.), 6.63 (d, 1H, J=7.3 Hz), 6.66 (d, 1H, J=8.5 Hz), 7.06 (brs, 1H, $D_2O$ exch.), 7.43 (t, 1H, J=7.8 Hz), 7.58 (m, 1H), 7.65 (t, 2H, J=7.2 Hz), 7.76-7.82 (m, 2H), 8.07 (d, 1H, J=8.4 Hz), 8.09-8.13 (m, 3H), 8.23 (d, 1H, J=8.4 Hz), 8.31 (d, 1H, J=8.4 Hz), 9.09 (m, 1H), 9.17 (m, 1H). $^{13}$C NMR (151 MHz, acetone-$d_6$) δ 27.42, 28.02, 38.46, 62.58, 68.02, 106.06, 106.69, 111.77, 112.29, 113.45, 119.09, 123.85, 124.04, 124.85, 127.44, 128.03, 130.11, 130.74, 131.92, 132.59, 133.47, 134.93, 140.19, 142.87, 147.48, 148.34, 151.46, 154.21. HR-MS (ESI) m/z: calcd for $C_{31}H_{29}N_6O$, $[M1+H]^+$=501.2397, found 501.2388. Anal. Calcd for $C_{31}H_{28}N_6O$: C, 74.38; H, 5.64; N, 16.79. Found: C, 74.53; H, 5.71; N, 16.61.

Detection of Senescent Cells

Comparative Example 1

In comparative example 1 the SBB histochemical dye was used to detect senescent cells in tissue sections by the histochemical method previously described [Georgakopoulou et al, Aging (Albany N.Y.) 2013].

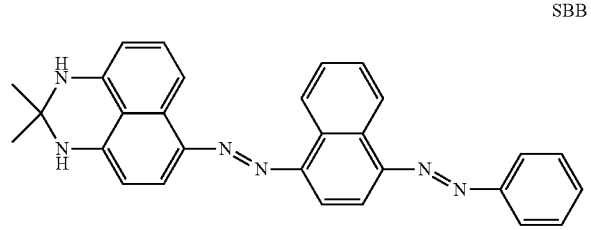 [SMILES: CC1(C)Nc2cccc3c(/N=N/c4ccc(/N=N/c5ccccc5)c5ccccc45)ccc(c23)N1]

SBB

Tissue sections were obtained from paraffin embedded, formalin fixed: (a) irradiated human laryngeal tumors and (b) mouse lung adenomas, with established presence of senescent cells [as described in Georgakopoulou et al, Aging (Albany N.Y.) 2013]. Subsequently, they were immobilized on glass microscopy slides by standard procedures and processed as follows:
  a. Deparaffinization for 5 min at room temperature in xylene.
  b. Gradual rehydration in solutions of descending concentration of ethanol (100%, 80%, 70%, 50% v/v) and finally in TBS (Tris-buffered saline) or PBS (Phosphate-buffered saline) solution.
  c. The SSB dye was diluted in 70% ethanol (v/v), filtered and then applied on tissue sections for 10 min.
  d. Quick wash in 50% (v/v) ethanol.
  e. Transfer and wash in TBS or PBS solution.
  f. Counterstain with Hematoxylin or Nuclear Fast Red, followed by mounting with glycerol and sealed with a cover slip.
  g. Microscopy observation.

Results from the application of the above described histochemical method are depicted in FIG. 1. Although senescent cells are clearly stained, the resolution of these cells require experienced pathologists. In addition, the necessity to have saturated ethanol-SBB solutions to achieve optimal performance for this staining process imposes practical difficulties during its application.

Comparative Example 2

In comparative example 2 the SBB histochemical dye was used to detect senescent cells in cell spreads by the histochemical method previously described [Georgakopoulou et al, Aging (Albany N.Y.) 2013].

Saos2-p53 Tet-On cells were grown on cover slips and collected after p53 induction to induce senescence. Cover slips were treated as follows:
  a. Fixation in ice-cold ethanol or methanol for 4 min.
  b. Application of SSB Dye, diluted in ethanol and filtered, on cells for 10 min.
  c. Quick wash in 50% (v/v) ethanol.
  d. Transfer and wash in TBS or PBS solution.
  e. Counterstain with Nuclear Fast Red, followed by mounting with glycerol and sealing with a cover slip.
  f. Microscopy observation.

Figure 2:
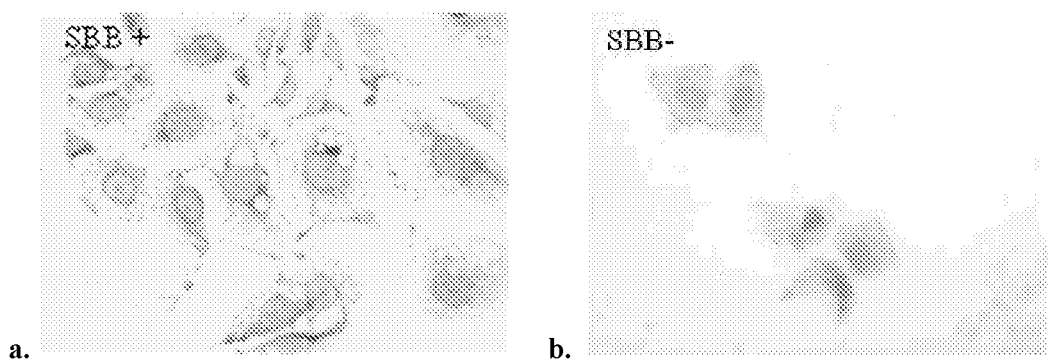
FIG. 2. Detection of senescent cells with SBB histochemical staining in cell culture. Induced Saos2-p53 Tet-On cells exhibiting senescence were stained with (a) SBB, or (b) only with Nuclear Fast Red (negative control).

Results from the application of the above described histochemical method are depicted in FIG. 2a. Although senescent cells are clearly stained, the resolution of these cells require experienced pathologists. In addition, the necessity to have saturated ethanol-SBB solutions to achieve optimal performance for this staining process imposes practical difficulties during its application.

Comparative Example 3

In comparative example 3 the SBB histochemical dye was used to detect lipofuscin rich cells in tissue sections by the histochemical method previously described [Georgakopoulou et al, Aging (Albany N.Y.) 2013].

Tissue sections were obtained from paraffin embedded, formalin fixed: (a) human seminal vesicle and (b) human liver with steatohepatitis that have high content of lipofusin making them ideal reference (control) tissues to test the SBB assay. Subsequently, they were immobilized on glass microscopy slides by standard procedures and processed as follows:
  a. Deparaffinization for 5 min at room temperature in xylene.
  b. Gradual rehydration in solutions of descending concentration of ethanol (100%, 80%, 70%, 50% v/v) and finally in TBS (Tris-buffered saline) or PBS (Phosphate-buffered saline) solution.
  c. The SSB dye was diluted in 70% ethanol (v/v), filtered and then applied on tissue sections for 10 min.
  d. Quick wash in 50% (v/v) ethanol.
  e. Transfer and wash in TBS or PBS solution.
  f. Counterstain with Hematoxylin or Nuclear Fast Red, followed by mounting with glycerol and sealed with a cover slip.
  g. Microscopy observation.

Figure 3:
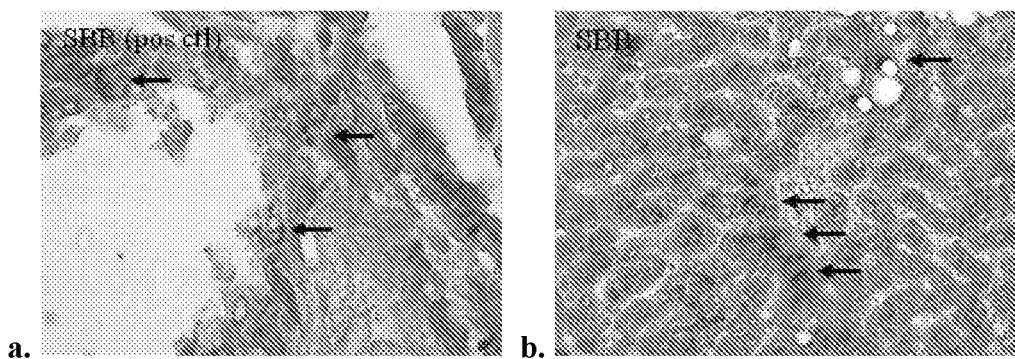
FIG. 3. Control experiments for lipofuscin detection using SBB staining in human (a) seminal vesicle and (b) liver with steatohepatitis, as reference tissues with high lipofuscin content. Arrows depict stained cells.

Results from the application of the above described histochemical method are depicted in FIG. 3.

Inventive Example 1

In the following example, compounds of the general formulae (3), (4), (6) and (7) prepared according to Examples 1 up to 4, and more specifically the derivative named as LG9 [(2-methyl-6-((E)-(4-((E)-phenyldiazenyl) naphthalen-1-yl)diazenyl)-2,3-dihydro-1H-perimidin-2-yl) methanol, its synthesis described at example 1] was used to detect senescent cells in tissue sections by the same histochemical method used for SBB staining.

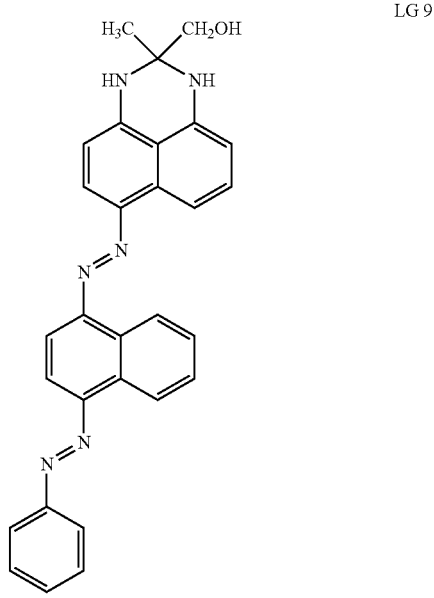 [SMILES: CC1(CO)Nc2cccc3c(/N=N/c4ccc(/N=N/c5ccccc5)c5ccccc45)ccc(c23)N1]

LG 9

Tissue sections were obtained from paraffin embedded, formalin fixed: (a) irradiated human laryngeal tumors and (b) mouse lung adenomas. Subsequently, they were immobilized on glass microscopy slides by standard procedures and processed as follows:
  a. Deparaffinization for 5 min at room temperature in xylene.
  b. Gradual rehydration in solutions of descending concentration of ethanol (100%, 80%, 70%, 50% v/v) and finally in TBS (Tris-buffered saline) or PBS (Phosphate-buffered saline) solution.
  c. The LG9 SBB-analogue was diluted in 70% ethanol (v/v), filtered and then applied on tissue sections for 10 min.
  d. Quick wash in 50% (v/v) ethanol.
  e. Transfer and wash in TBS or PBS solution.
  f. Counterstain with Hematoxylin or Nuclear Fast Red, followed by mounting with glycerol and sealed with a cover slip.
  g. Microscopy observation.

Figure 4:
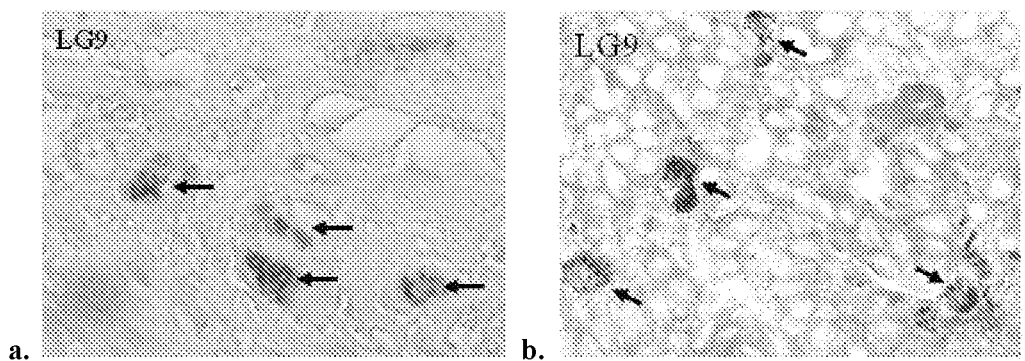
FIG. 4. Detection of senescent cells with the LG9 compound with histochemical staining in tissue sections from (a) irradiated human laryngeal tumors, and (b) mouse lung adenomas, with established presence of senescent cells. Arrows depict stained senescent cells.

Representative results from the application of the above described histochemical method using the novel compound LG9 are depicted in FIGS. 4a,b. The above histochemical method using the novel SBB analogue LG9 does not encounter the ethanol solubility problems that the SBB stain exhibits [Georgakopoulou et al, Aging (Albany N.Y.) 2013]. In addition, it provides similar and even better resolution of senescent cells in comparison to the SBB staining shown in FIGS. 1a,b and 2a. This makes easier the application of this method and the recognition of senescent cells, making this method a choice for many researchers and non-researchers, avoiding experienced personnel, like pathologists.

Inventive Example 2

In inventive example 2, the derivative compound LG9 was used to detect senescent cells in cell spreads by the same histochemical method used for SBB staining [Georgakopoulou et al, Aging (Albany N.Y.) 2013].

Saos2-p53 Tet-On cells were grown on cover slips and collected without after p53 induction to induce senescence. Cover slips were treated as follows:
  a. Fixation in ice-cold ethanol or methanol for 4 min.
  b. Application of the LG9 SBB-analogue, diluted in ethanol and filtered, on cells for 10 min.
  c. Quick wash in 50% (v/v) ethanol.
  d. Transfer and wash in TBS or PBS solution.
  e. Counterstain with Nuclear Fast Red, followed by mounting with glycerol and sealing with a cover slip.
  f. Microscopy observation.

Figure 5:
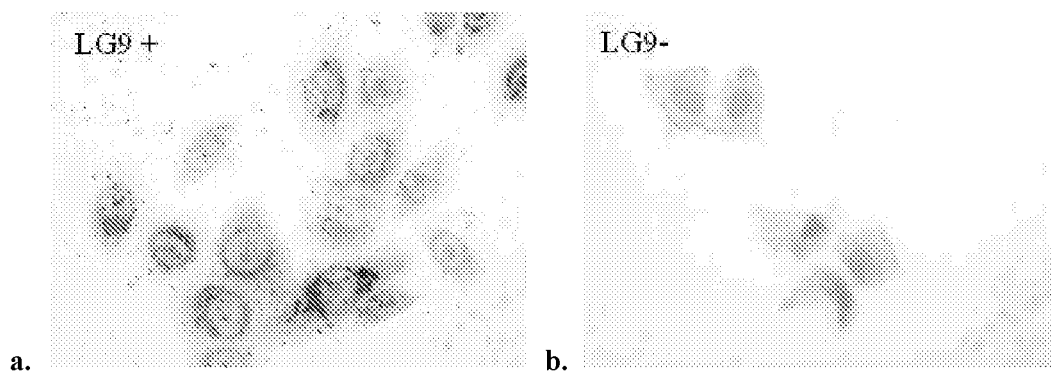
FIG. 5. Detection of senescent cells with the SBB-analogue compound LG9 using histochemical staining in cell culture. Induced Saos2-p53 Tet-On cells exhibiting senescence were stained with (a) LG9, or (b) only with Nuclear Fast Red (negative control).

Representative results from the application of the above described histochemical method using the novel compound LG9 is depicted in FIG. 5a.

It should be noted that the above histochemical method using the novel SBB analogue LG9 does not encounter the ethanol solubility problems that the SBB stain exhibits [Georgakopoulou et al, Aging (Albany N.Y.) 2013]. In addition, it provides similar and even better resolution of senescent cells in comparison to the SBB staining shown in FIGS. 1a,b and 2a. This makes easier the application of this method and the recognition of senescent cells, making this method a choice for many researchers and non-researchers, avoiding experienced personnel, like pathologists.

The ease of use makes it ideal for application in the following fields: biomedical research, clinical/health care, cosmetics, male and female infertility/subfertillity, animal farming and the food industry. Routine detection of senescent cells can be achieved in: i) tissues of animal origin, ranging from invertebrates to mammals, including humans, ii) single animal cells either derived from the above tissues or in suspensions, body fluids and cell scrapes/smears, for example blood samples, urine specimens or cervical smears, or in laboratory culture. All these biological materials can be either in a fresh or preserved state (e.g. by physical or chemical means, such as freezing or formaldehyde treatment) as well as embedded in inert supportive material, like paraffin.

Inventive Example 3

In inventive example 3 the derivative compound LG9 was used to detect lipofuscin rich cells in tissue sections by the histochemical method previously described [Georgakopoulou et al, Aging (Albany N.Y.) 2013].

Tissue sections were obtained from paraffin embedded, formalin fixed: (a) human seminal vesicle and (b) human liver with steatohepatitis that have high content of lipofusin making them ideal reference (control) tissues to test the performance of the LG9 compound. Subsequently, they were immobilized on glass microscopy slides by standard procedures and processed as follows:
  a. Deparaffinization for 5 min at room temperature in xylene.
  b. Gradual rehydration in solutions of descending concentration of ethanol (100%, 80%, 70%, 50% v/v) and finally in TBS (Tris-buffered saline) or PBS (Phosphate-buffered saline) solution.
c. The LG9 SBB-analogue was diluted in 70% ethanol (v/v), filtered and then applied on tissue sections for 10 min.
d. Quick wash in 50% (v/v) ethanol.
e. Transfer and wash in TBS or PBS solution.
f. Counterstain with Hematoxylin or Nuclear Fast Red, followed by mounting with glycerol and sealed with a cover slip.
g. Microscopy observation.

Figure 6:
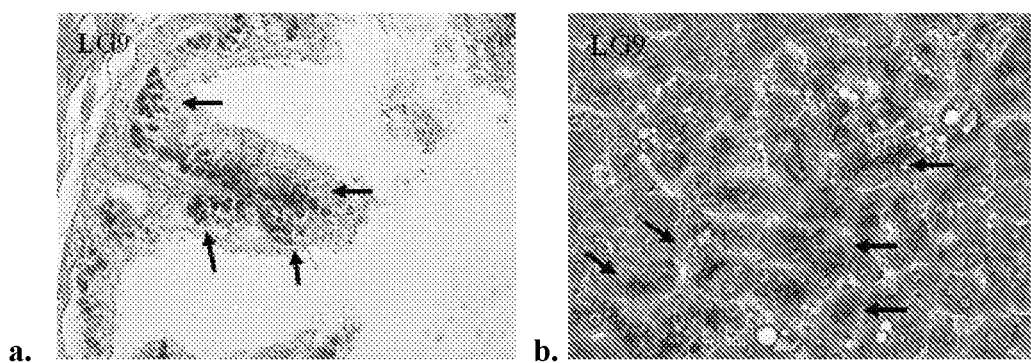
FIG. 6. Control experiments for the specific reaction of compound LG9 with lipofuscin in human (a) seminal vesicle and (b) liver with steatohepatitis, as reference tissues with high lipofuscin content. Arrows depict stained cells.

Results from the application of the above described histochemical method are depicted in FIG. 6.

Inventive Example 4

In inventive example 4 the derivative compound LG9 was used to detect lipofuscin rich cells in tissue sections by the histochemical method previously described [Georgakopoulou et al, Aging (Albany N.Y.) 2013].

Tissue sections were obtained from paraffin embedded, formalin fixed, human thymus and specifically from the cortex and medulla of this organ. Subsequently, they were immobilized on glass microscopy slides by standard procedures and processed as follows:
a. Deparaffinization for 5 min at room temperature in xylene.
b. Gradual rehydration in solutions of descending concentration of ethanol (100%, 80%, 70%, 50% v/v) and finally in TBS (Tris-buffered saline) or PBS (Phosphate-buffered saline) solution.
c. The LG9 SBB-analogue was diluted in 70% ethanol (v/v), filtered and then applied on tissue sections for 10 min.
d. Quick wash in 50% (v/v) ethanol.
e. Transfer and wash in TBS or PBS solution.
f. Counterstain with Hematoxylin or Nuclear Fast Red, followed by mounting with glycerol and sealed with a cover slip.
g. Microscopy observation.

Figures 7, 8:
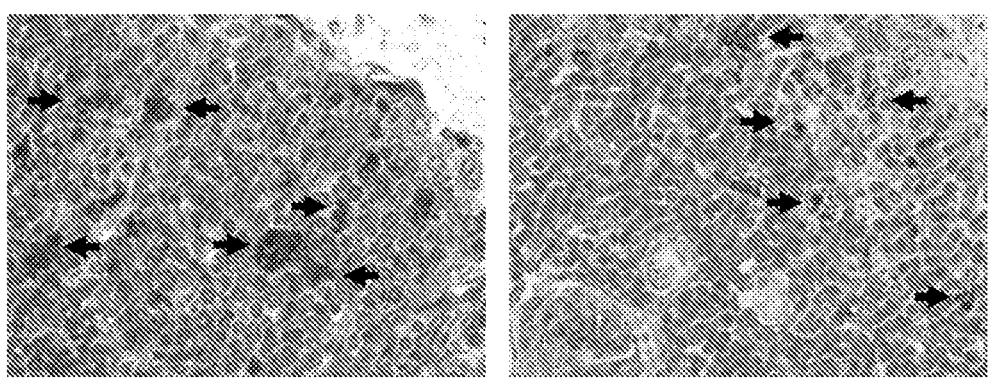
FIG. 7. Detection of senescent cells with the LG9 compound with histochemical staining in tissue sections from the cortex and medulla of the human thymus. Arrows depict stained senescent cells.
FIG. 8. Detection of senescent cells with the LG46 (Example 3) and LG48 (Example 4) compounds with histochemical staining in liver tissue sections. Arrows depict stained cells.

Results from the application of the above described histochemical method are depicted in FIG. 7. The human thymus is an interesting model of investigation since this organ undergoes involution starting from early childhood, with many autoimmunity disorders steming from its dysfunction (Wayne et al 2007). Considering various unresolved issues regarding its physiology and pathology, all potentially involving senescence, the staining procedures developed in the current proposal will provide the, lacking until now, necessary tools to answer such matters.

Inventive Example 5

In the following example, compounds of the general formulae (11) and (14), and more specifically the derivatives named as LG46 [3-((E)-(4-((E)-(2,2-dimethyl-2,3-dihydro-1H-perimidin-6-yl)diazenyl)naphthalen-1-yl)diazenyl)phenol] and LG48 [2-(4-((E)-(4-((E)-(2,2-dimethyl-2,3-dihydro-1H-perimidin-6-yl)diazenyl)naphthalen-1-yl) diazenyl)phenyl)ethanol] prepared according to Examples 3 up to 4, were used to detect senescent cells in tissue sections by the same histochemical method used for SBB staining.

Tissue sections were obtained from paraffin embedded, formalin fixed liver biopsies that have high content of lipofusin. Subsequently, they were immobilized on glass microscopy slides by standard procedures and processed as follows:

a. Deparaffinization for 5 min at room temperature in xylene.
b. Gradual rehydration in solutions of descending concentration of ethanol (100%, 80%, 70%, 50% v/v) and finally in TBS (Tris-buffered saline) or PBS (Phosphate-buffered saline) solution.
c. The LG46 or LG48 analogue was diluted in 70% ethanol (v/v), filtered and then applied on tissue sections for 10 min.
d. Quick wash in 50% (v/v) ethanol.
e. Transfer and wash in TBS or PBS solution.
f. Counterstain with Hematoxylin or Nuclear Fast Red, followed by mounting with glycerol and sealed with a cover slip.
g. Microscopy observation.

Representative results from the application of the above described histochemical method using the novel compound LG46 and LG48 are depicted in FIGS. 8a,b. The above histochemical method using these novel analogues does not encounter the ethanol solubility problems that the SBB stain exhibits [Georgakopoulou et al, Aging (Albany N.Y.) 2013]. In addition, it provides similar and even better resolution of senescent cells in comparison to the SBB staining shown in FIGS. 1a,b and 2a. This makes easier the application of this method and the recognition of senescent cells, making this method a choice for many researchers and non-researchers, avoiding experienced personnel, like pathologists.

REFERENCES

Gorgoulis V G, Halazonetis T D. Curr Opin Cell Biol 2010, 22: 816-827.
Dimri G P, et al. Proc Natl Acad Sci USA 1995. 92: 9363-9367.
Chen Q M. Ann N Y Acad Sci 2000, 908: 111-125.
Rodier F, Campisi J. J. Cell Biol 2011, 192: 547-556.
Bartkova J, et al. Nature. 2006, 444: 633-637.
Halazonetis T D, et al. Science 2008, 319: 1352-1355.
Dirmi G P, Campisi J, Peacocke M. U.S. Pat. No. 5,491,069 A, U.S. Ser. No. 08/198,436, 1996.
Dirmi G P, Campisi J, Peacocke M. U.S. Pat. No. 5,795,728 A, U.S. Ser. No. 08/479,082, 1996.
Liontos M, et al. Cancer Res 2007, 67: 10899-909.
Liontos M, et al. Am J Pathol 2009, 175: 376-391.
Shay J W, Roninson I B. Oncogene 2004, 23: 2919-2933.
Collado M, Serrano M. Nat Rev Cancer 2006, 6: 472-476.
de Jesus B B, Blasco M A. Circ Res 2012, 111: 97-109.
Cairney C J, et al. Drug Discov Today 2012, 17: 269-276.
Collado M, Serrano M. Nat Rev Cancer 2010, 10:51-57.
Debacq-Chainiaux F, et al. Nat Protoc 2009, 4: 1798-1806.
Severino J, et al. Exp Cell Res 2000, 257:162-171.
Binet R, et al. Cancer Res 2009, 69: 9183-9191.
Georgakopoulou E, et al. Aging (Albany N.Y.) 2013, 5: 37.
Jung T, et al. Methods Mol Biol 2010, 594: 173-193.
Jung T, et al. Ann N Y Acad Sci 2007, 1119: 97-111.
Brunk U T, Terman A. Free Radic Biol Med 2002, 33: 611-619.
Hohn A, et al. Free Radic Biol Med 2010, 48: 1100-1108.
Dowson J H, Harris S J. J Microsc 1981, 123: 249-258.
Jung T A H, Grune T. 2010. Advanced Protocols in Oxidative Stress II, Methods in Molecular Biology. D. Armstrong, editor: Humana Press
Charles C. 2002. Theory and Practice of Histological Techniques. GM Bancroft JD editor: Churchill Livingstone.
Glees P, Hasan M. Norm Pathol Anat (Stuttg) 1976, 32: 1-68.
Robles L J. Mech Ageing Dev 1978, 7: 53-64.

Zhang J, Zhang S. Synth Comm 2007, 37: 2615-2624.
Farrand L D et al Merck Patent GmbH WO 2014/111112 A1.
Wayne A. Mitchell and Richard Aspinall (2007). Chapter: Immunosenescence, Thymic Involution and Autoimmunity in Immunosenescence, Part of the series Medical Intelligence Unit pp 68-79

The invention claimed is:

1. A compound that functions as a senescent cell detector of the general formula (2), shown below:

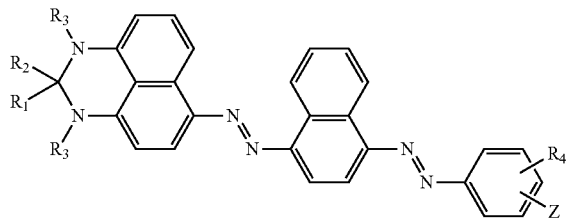

(2)

wherein:
  $R_1$ and $R_2$ are each independently selected from:
    i) hydrogen, with the proviso that only one of $R_1$ and $R_2$ can be hydrogen in general structure (2) above,
    ii) an optionally substituted (1-10C)alkyl group;
    iii) an optionally substituted aryl group;
    iv) an optionally substituted (1-10C)alkyl-aryl group;
    v) an optionally substituted aryl-(1-10C)alkyl group; or
    vi) $R_1$ and $R_2$ are linked so as to form part of a spiranic cycloalkane group, selected from cyclopentyl, cyclohexyl, cycloheptyl, cyclooctyl, cyclononyl or adamantanyl;
  $R_3$ is hydrogen or (1-10C)alkyl group;
  $R_4$ is hydrogen, or one or more of the following substituents:
    i) a halogen selected from F, Cl, Br and I;
    ii) $NO_2$;
    iii) $CF_3$;
    iv) $SCH_3$;
    v) an optionally substituted (1-5C)alkyl group;
    vi) a (1-10C)alkoxy group which optionally comprises one or more heteroatoms; and
  Z is either $Z_1$ or —Ar—$Z_1$; and $Z_1$ is selected from OH, $NH_2$, $O(CH_2)_nCH_2OH$, $(CH_2)_qOH$ or COOH, wherein n is an integer selected from 1 to 9, and wherein q is an integer selected from 1 to 4, and wherein Ar is an aryl group optionally substituted with one or more of the following substituents halogen, (1-6C)alkyl, (1-6C)alkenyl or (1-5C)alkoxy; and wherein, unless otherwise specified, optionally substituted refers to the optional substitution by one or more substituents selected from the group consisting of halo, trifluoromethyl, trifluoromethoxy, amino, cyano, hydroxy, carboxy, carbamoyl, sulphamoyl, aryl, heteroaryl, (1-6C)alkyl, (3-8C)cycloalkyl and (1-6C)alkoxy.

2. The compound according to claim 1, wherein the compound is of the general formula (2b), shown below:

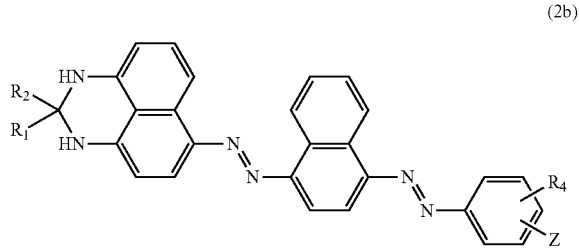

(2b)

wherein,
  $R_1$ and $R_2$ are each independently selected from:
    i) hydrogen, with the proviso that only one of $R_1$ and $R_2$ can be hydrogen in general structure (2b) above;
    ii) a (1-4C)alkyl group; or
    iii) an aryl group;
  $R_4$ is hydrogen, or one or more of the following substituents:
    i) a halogen selected from F, Cl, Br and I;
    ii) $NO_2$;
    iii) $CF_3$;
    iv) $SCH_3$;
    v) an optionally substituted (1-5C)alkyl group;
    vi) a (1-10C)alkoxy group which optionally comprises one or more heteroatoms; and
  Z is either $Z_1$ or Ar—$Z_1$, and $Z_1$ is selected from —OH or —$NH_2$, wherein Ar is an aryl group optionally substituted with one or more of the following substituents halogen, (1-4C)alkyl, (1-4C)alkenyl or (1-4C)alkoxy, wherein, unless otherwise specified, optionally substituted refers to the optional substitution by one or more substituents selected from the group consisting of halo, trifluoromethyl, trifluoromethoxy, amino, cyano, hydroxy, carboxy, carbamoyl, sulphamoyl, aryl, heteroaryl, (1-6C)alkyl, (3-8C)cycloalkyl and (1-6C)alkoxy.

3. The compound according to claim 2, wherein $R_4$ is hydrogen, or one or more of the following substituents:
  i) a halogen selected from F, Cl, Br and I, preferably F or Cl;
  ii) $NO_2$;
  iii) $CF_3$;
  iv) a (1-5C)alkyl group; or
  v) a (1-5C)alkoxy group.

4. The compound according to claim 2, wherein Z is either $Z_1$ or Ar—$Z_1$, and $Z_1$ is —OH and Ar is a phenyl group.

5. The compound according to claim 1, wherein the compound is of the general formula (5), shown below:

(5)

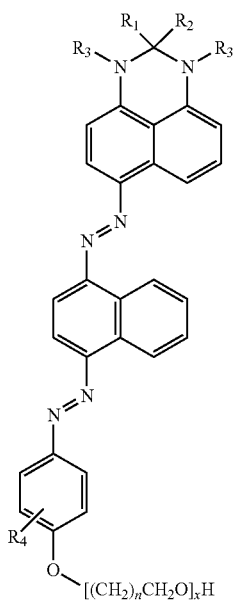

wherein:
  x is an integer selected from 0 or 1;
  n is an integer selected from 1 to 9;
  $R_1$ and $R_2$ are each independently selected from:
    i) hydrogen, provided that at least one of $R_1$, $R_2$ is other than hydrogen;
    ii) an optionally substituted (1-10C)alkyl group;
    iii) an optionally substituted aryl group;
    iv) an optionally substituted (1-10C)alkyl-aryl group;
    v) an optionally substituted aryl-(1-10C)alkyl group; or
    vi) $R_1$ and $R_2$ are linked so as to form part of a spiranic cycloalkane group, selected from cyclopentyl, cyclohexyl, cycloheptyl, cyclooctyl, cyclononyl or adamantanyl;
  $R_3$ is hydrogen or (1-10C)alkyl group; and
  $R_4$ is hydrogen, or one or more of the following substituents:
    i) a halogen selected from F, Cl, Br and I;
    ii) $NO_2$;
    iii) $CF_3$;
    iv) $SCH_3$;
    v) an optionally substituted (1-5C)alkyl group; or
    vi) a (1-10C)alkoxy group which optionally comprises one or more heteroatoms;
  wherein, unless otherwise specified, optionally substituted refers to the optional substitution by one or more substituents selected from the group consisting of halo, trifluoromethyl, trifluoromethoxy, amino, cyano, hydroxy, carboxy, carbamoyl, sulphamoyl, aryl, heteroaryl, (1-6C)alkyl, (3-8C)cycloakyl and (1-6C) alkoxy.

6. The compound according to claim 1, wherein the compound is of the general formula (6), shown below:

(6)

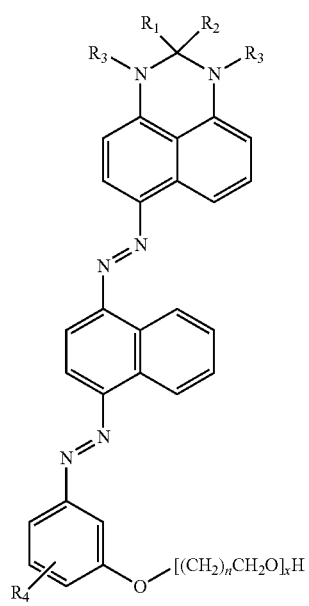

wherein:
  x is an integer selected from 0 or 1;
  n is an integer selected from 1 to 9;
  $R_1$ and $R_2$ are each independently selected from:
    i) hydrogen, provided that at least one of $R_1$, $R_2$ is other than hydrogen;
    ii) an optionally substituted (1-10C)alkyl group;
    iii) an optionally substituted aryl group;
    iv) an optionally substituted (1-10C)alkyl-aryl group;
    v) an optionally substituted aryl-(1-10C)alkyl group; or
    vi) $R_1$ and $R_2$ are linked so as to form part of a spiranic cycloalkane group, selected from cyclopentyl, cyclohexyl, cycloheptyl, cyclooctyl, cyclononyl or adamantanyl;
  $R_3$ is hydrogen or (1-10C)alkyl group; and
  $R_4$ is hydrogen, or one or more of the following substituents:
    i) a halogen selected from F, Cl, Br and I;
    ii) $NO_2$;
    iii) $CF_3$;
    iv) $SCH_3$;
    v) an optionally substituted (1-5C)alkyl group; or
    vi) a (1-10C)alkoxy group which optionally comprises one or more heteroatoms;
  wherein unless otherwise specified, optionally substituted refers to the optional substitution by one or more substituents selected from the group consisting of halo, trifluoromethyl, trifluoromethoxy, amino, cyano, hydroxy, carboxy, carbamoyl, sulphamoyl, aryl, heteroaryl, (1-6C)alkyl, (3-8C)cycloalkyl and (1-6C) alkoxy.

7. The compound according to claim 1, wherein the compound is of the general formula (7), shown below:

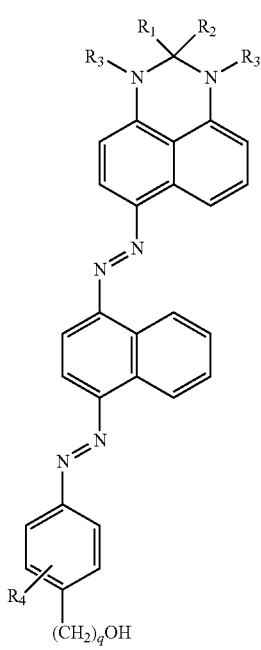

(7)

wherein:

q is an integer selected from 1 to 4;

$R_1$ and $R_2$ are each independently selected from:

i) hydrogen, provided that at least one of $R_1$, $R_2$ is other than hydrogen;

ii) an optionally substituted (1-10C)alkyl group;

iii) an optionally substituted aryl group;

iv) an optionally substituted (1-10C)alkyl-aryl group;

v) an optionally substituted aryl—(1-10C)alkyl group; or vi) $R_1$ and $R_2$ are linked so as to form part of a spiranic cycloalkane group, selected from cyclopentyl, cyclohexyl, cycloheptyl, cyclooctyl, cyclononyl or adamantanyl;

$R_3$ is hydrogen or (1-10C)alkyl group; and $R_4$ is hydrogen, or one or more of the following substituents:

i) a halogen selected from F, Cl, Br and I;

ii) $NO_2$;

iii) $CF_3$;

iv) $SCH_3$;

v) an optionally substituted (1-5C)alkyl group; or vi) a (1-10C)alkoxy group which optionally comprises one or more heteroatoms;

wherein, unless otherwise specified, optionally substituted refers to the optional substitution by one or more substituents selected from the group consisting of halo, trifluoromethyl, trifluoromethoxy, amino, cyano, hydroxy, carboxy, carbamoyl, sulphamoyl, aryl, heteroaryl, (1-6C)alkyl, (3-8C)cycloalkyl and (1-6C)alkoxy.

8. The compound according to claim 1, wherein the compound is of the general formula (8), shown below:

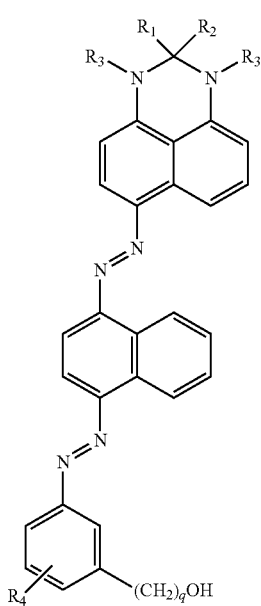

(8)

wherein:

q is an integer selected from 1 to 4;

$R_1$ and $R_2$ are each independently selected from:

i) hydrogen, provided that at least one of $R_1$, $R_2$ is other than hydrogen;

ii) an optionally substituted (1-10C)alkyl group;

iii) an optionally substituted aryl group;

iv) an optionally substituted (1-10C)alkyl-aryl group;

v) an optionally substituted aryl—(1-10C)alkyl group; or vi) $R_1$ and $R_2$ are linked so as to form part of a spiranic cycloalkane group, selected from cyclopentyl, cyclohexyl, cycloheptyl, cyclooctyl, cyclononyl or adamantanyl;

$R_3$ is hydrogen or (1-10C)alkyl group; and $R_4$ is hydrogen, or one or more of the following substituents:

i) a halogen selected from F, Cl, Br and I;

ii) $NO_2$;

iii) $CF_3$;

iv) $SCH_3$;

v) an optionally substituted (1-5C)alkyl group; or vi) a (1-10C)alkoxy group which optionally comprises one or more heteroatoms;

wherein, unless otherwise specified, optionally substituted refers to the optional substitution by one or more substituents selected from the group consisting of halo, trifluoromethyl, trifluoromethoxy, amino, cyano, hydroxy, carboxy, carbamoyl, sulphamoyl, aryl, heteroaryl, (1-6C)alkyl (3-8C)cycloalkyl and (1-6C) alkoxy.

9. A compound being selected from any one of the following:

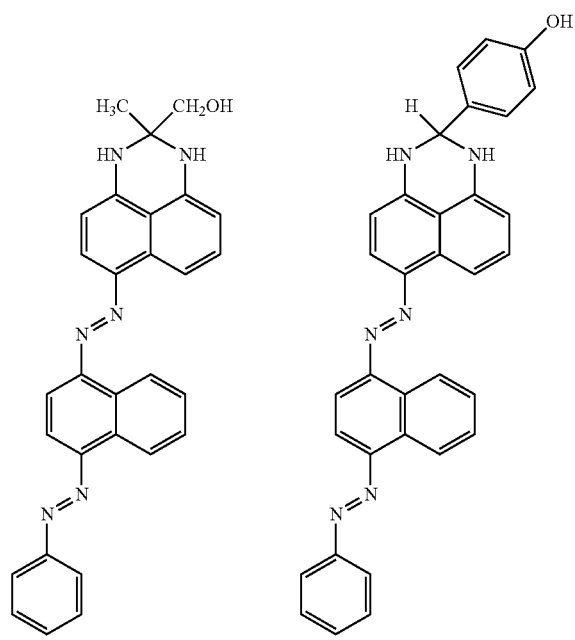
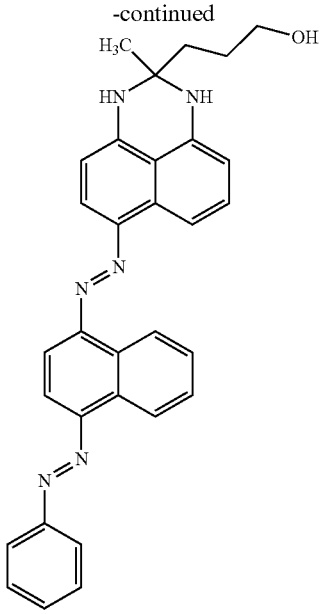
10. The compound according to claim 9, being selected from any one of the following:
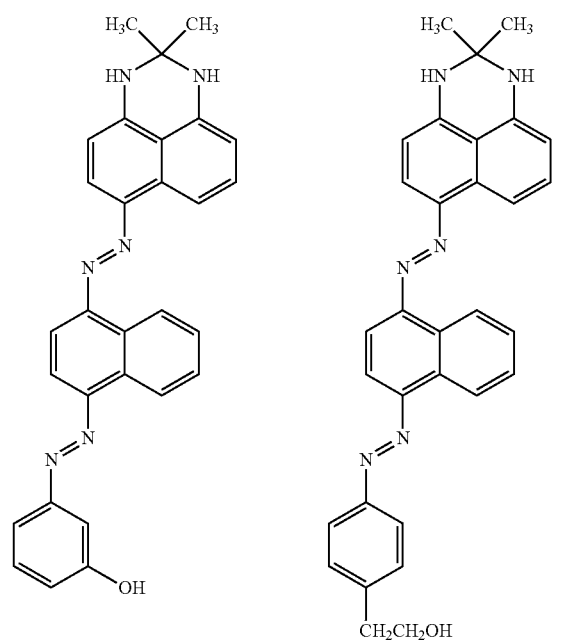
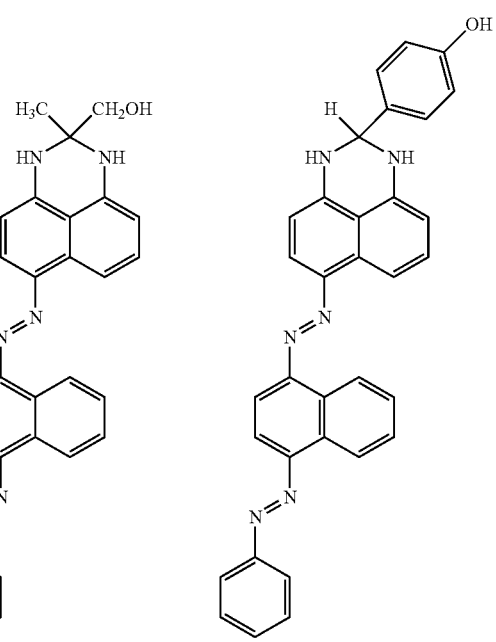

11. A process for the preparation of a compound of formula (2) according to claim 1, comprising reacting a compound of formula B:

(B)

with a compound of formula Y, shown below:

(Y)

wherein Z and $R_1$ to $R_4$ are as defined in claim 1.

12. A method for detecting senescence, comprising contacting a compound of the general formula (1) or (2) with a sample of single or mixed cells, optionally in the presence of lipofuscin:

(1)

(2)

wherein:
- $R_1$ and $R_2$ are each independently selected from:
  - i) hydrogen, with the proviso that $R_2$ is not hydrogen in general structure (1) above and only one of $R_1$ and $R_2$ can be hydrogen in general structure (2) above,
  - ii) an optionally substituted (1-10C)alkyl group;
  - iii) an optionally substituted aryl group;
  - iv) an optionally substituted (1-10C)alkyl-aryl group;
  - v) an optionally substituted aryl—(1-10C)alkyl group: or
  - vi) $R_1$ and $R^2$, are linked so as to form part of a spiranic cycloalkane group, selected from cyclopentyl, cyclohexyl, cycloheptyl, cyclooctyl, cyclononyl or adamantanyl;
- $R_3$ is hydrogen or (1-10C) alkyl group;
- $R_4$ is hydrogen, or one or more of the following substituents:
  - i) a halogen selected from F, Cl, Br and I:
  - ii) $NO_2$;
  - iii) $CF_3$;
  - iv) $SCH_3$;
  - v) an optionally substituted (1-5C)alkyl group:
  - vi) a(1-10C)alkoxy group which optionally comprises one or more heteroatoms; and
- Z is either $Z_1$ or —Ar—$Z_1$—and $Z_1$ is selected from OH, $NH_2$, $O(CH_2)_0CH_2OH$, $(CH_2)_0OH$ or COOH, wherein n is an integer selected from 1 to 9, and wherein q is an integer selected from 1 to 4 and wherein Ar is an aryl group optionally substituted with one or more of the following substituents halogen, (1-6C)alkyl, (1-6C)alkenyl or (1-5C)alkoxy; and wherein, unless otherwise specified, optionally substituted refers to the optional substitution by one or more substituents selected from the group consisting of halo, trifluoromethyl, trifluoromethoxy, amino, cyano, hydroxy, carboxy, carbamoyl, sulphamoyl, aryl, heteroaryl, (1-6C)alkyl, (3-8C)cycloalkyl and (1-6C) alkoxy.

13. The method for detecting senescence according to claim 12, wherein the single or mixed of cells are from tissue samples of animal origin.

14. The method for detecting senescence according to claim 13, wherein the tissue sample is of human origin.

15. A kit for detecting senescence and differentiating senescent cells comprising:
 a. a compound according to claim 1; and
 b. one or more additional reagents required for detecting senescence in a sample of single or mixed cells.

16. The method for detecting senescence according to claim 12, wherein the compound is of the general formula (1b) or (2b), shown below:

(1b)

(2b)

wherein,
 $R_1$ and $R_2$ are each independently selected from:
  i) hydrogen, with the proviso that $R_2$ is not hydrogen in general structure (1b) above and only one of $R_1$ and $R_2$ can be hydrogen in general structure (2b) above,
  ii) a (1-4C)alkyl group; or
  iii) an aryl group;
 $R_4$ is hydrogen, or one or more of the following substituents:
  i) a halogen selected from F, Cl, Br and I;
  ii) $NO_2$;
  iii) $CF_3$;
  iv) $SCH_3$;
  v) an optionally substituted (1-5C)alkyl group;
  vi) a (1-10C)alkoxy group which optionally comprises one or more heteroatoms; and
 Z is either $Z_1$ or Ar—$Z_1$, and $Z_1$ is selected from —OH or —$NH_2$, wherein Ar is an aryl group optionally substituted with one or more of the following substituents halogen, (1-4C)alkyl, (1-4C)alkenyl or (1-4C)alkoxy;
 wherein, unless otherwise specified, optionally substituted refers to the optional substitution by one or more substituents selected from the group consisting of halo, trifluoromethyl, trifluoromethoxy, amino, cyano, hydroxy, carboxy, carbamoyl, sulphamoyl, aryl, heteroaryl, (1-6C)alkyl, (3-8C)cycloalkyl and (1-6C) alkoxy; and
 provided that the compound is not 2-(2—Methyl—6-((E)-(4-((E)—phenyldiazenyl) naphthalen—1-yl)diazenyl)—2,3—dihydro—1H—perimidin—2-yl)ethanol.

17. The method of detecting senescence according to claim 16, wherein $R_4$ is hydrogen, or one or more of the following substituents:
 i) a halogen selected from F, Cl, Br and I, preferably F or Cl;
 ii) $NO_2$;
 iii) $CF_3$,
 iv) a (1-5C)alkyl group; or
 v) a (1-5C)alkoxy group.

18. The method of detecting senescence according to claim 16, wherein $R_4$ is hydrogen.

19. The method of detecting senescence according to claim 16, wherein Z is either $Z_1$ or Ar—$Z_1$, and $Z_1$ is —OH and Ar is a phenyl group.

20. The method of detecting senescence according to claim 12, wherein the compound is of the general formula (3), shown below:

(3)

wherein:
 $R_1$ is a (1-10C)alkyl;
 $R_2$ is selected from:
  i) an optionally substituted (1-8C)alkyl group;
  ii) an optionally substituted aryl group; or
  iii) an optionally substituted (1-5C)alkyl-aryl group;
 $R_3$ is hydrogen or (1-10C)alkyl group; and
 $R_4$ is hydrogen, or one or more of the following substituents:
  i) a halogen selected from F, Cl, Br and I;
  ii) $NO_2$;
  iii) $CF_3$;
  iv) $SCH_3$;
  v) an optionally substituted (1-5C)alkyl group; or
  vi) a (1-10C)alkoxy group which optionally comprises one or more heteroatoms; and
 wherein, unless otherwise specified, optionally substituted refers to the optional substitution by one or more substituents selected from the group consisting of halo, trifluoromethyl, trifluoromethoxy, amino, cyano, hydroxy, carboxy, carbamoyl, sulphamoyl, aryl, heteroaryl, (1-6C)alkyl, (3-8C)cycloalkyl and (1-6C) alkoxy.

21. The method of detecting senescence according to claim 20, wherein $R_3$ is hydrogen.

22. The method of detecting senescence according to claim 20, wherein $R_1$ is a (1-4C)alkyl and $R_2$ is:
 i) a (1-4C)alkyl group; or
 ii) an aryl group.

23. The method of detecting senescence according to claim 12, wherein the compound is of the general formula (4), shown below:

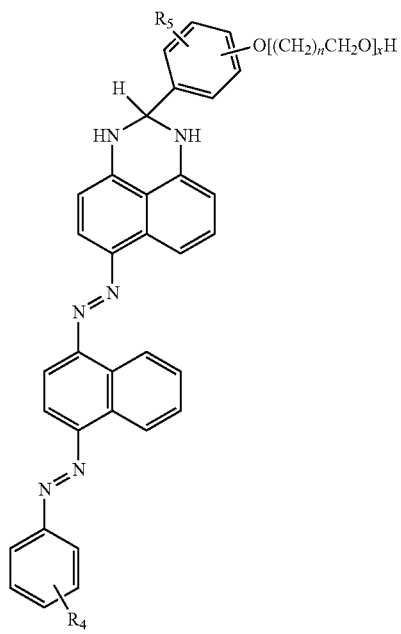
(4)

wherein:

x is an integer selected from 0 or 1;

n is an integer selected from 1 to 9;

$R_4$ is hydrogen, or one or more of the following substituents:
 i) a halogen selected from F, Cl, Br and I;
 ii) $NO_2$;
 iii) $CF_3$,
 iv) $SCH_3$;
 v) an optionally substituted (1-5C)alkyl group; or
 vi) a (1-10C)alkoxy group which optionally comprises one or more heteroatoms; and $R_5$ is hydrogen, or one or more of the following substituents:
 i) a halogen selected from F, Cl, Br and I;
 ii) a (1-6C)alkyl or (1-6C)alkenyl group; or
 iii) a (1-5C)alkoxy group; and wherein, unless otherwise specified, optionally substituted refers to the optional substitution by one or more substituents selected from the group consisting of halo, trifluoromethyl, trifluoromethoxy, amino, cyano, hydroxy, carboxy, carbamoyl, sulphamoyl, aryl, heteroaryl, (1-6C)alkyl, (3-8C)cycloalkyl and (1-6C)alkoxy.

24. The method of detecting senescence according to claim 12, wherein the compound is of the general formula (5), (6), (7) or (8) shown below:

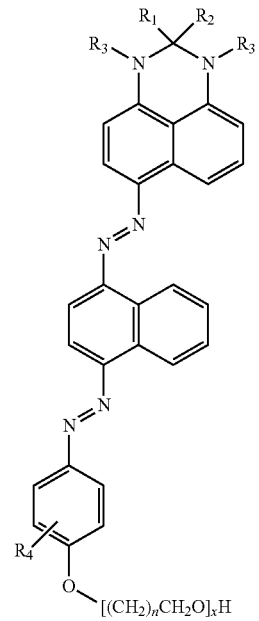
(5)

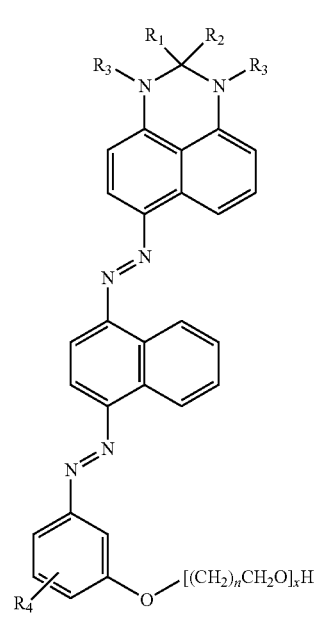
(6)

-continued

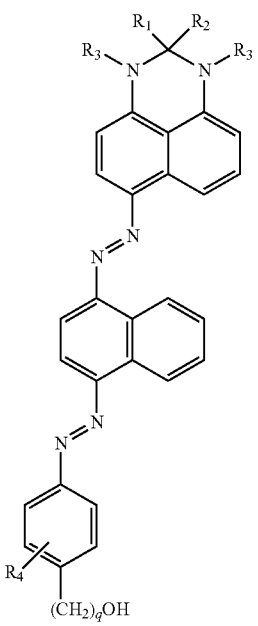
(7)

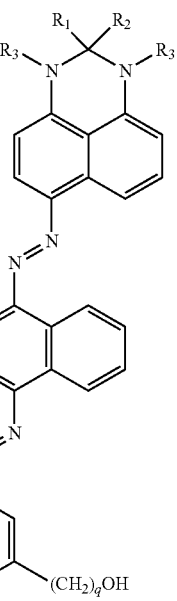
(8)

wherein:

x is an integer selected from 0 or 1;

n is an integer selected from 1 to 9;

q is an integer selected from 1 to 4;

$R_1$ and $R_2$ are each independently selected from:

i) hydrogen, provided that at least one of $R_1$, $R_2$ is other than hydrogen;

ii) an optionally substituted (1-10C)alkyl group;

iii) an optionally substituted aryl group;

iv) an optionally substituted (1-10C)alkyl-aryl group;

v) an optionally substituted aryl-(1-10C)alkyl group; or vi) $R_1$ and $R_2$ are linked so as to form part of a spiranic cycloalkane group, selected from cyclopentyl, cyclohexyl, cycloheptyl, cyclooctyl, cyclononyl or adamantanyl;

$R_3$ is hydrogen or (1-10C)alkyl group; and $R_4$ is hydrogen, or one or more of the following substituents:

i) a halogen selected from F, Cl, Br and I;

ii) $NO_2$;

iii) $CF_3$;

iv) $SCH_3$;

v) an optionally substituted (1-5C)alkyl group; or vi) a (1-10C)alkoxy group which optionally comprises one or more heteroatoms; and wherein, unless otherwise specified, optionally substituted refers to the optional substitution by one or more substituents selected from the group consisting of halo, trifluoromethyl, trifluoromethoxy, amino, cyano, hydroxy, carboxy, carbamoyl, sulphamoyl, aryl, heteroaryl, (1-6C)alkyl, (3-8C)cycloalkyl and (1-6C)alkoxy.

* * * * *

UNITED STATES PATENT AND TRADEMARK OFFICE
CERTIFICATE OF CORRECTION

PATENT NO. : 10,947,390 B2  
APPLICATION NO. : 16/313617  
DATED : March 16, 2021  
INVENTOR(S) : Vassilis Gorgoulis et al.

Page 1 of 1

It is certified that error appears in the above-identified patent and that said Letters Patent is hereby corrected as shown below:

In the Claims

<u>Column 66, Claim 12, Line 46:</u>  
"a(1-10C)alkoxy" should read: --a (1-10C)alkoxy--.

<u>Column 66, Claim 12, Line 49:</u>  
"$O(CH_2)_oCH_2OH, (CH_2)_oOH$ or" should read: --$O(CH_2)_nCH_2OH, (CH_2)_qOH$ or--.

Signed and Sealed this  
Fifth Day of October, 2021

Drew Hirshfeld  
*Performing the Functions and Duties of the*  
*Under Secretary of Commerce for Intellectual Property and*  
*Director of the United States Patent and Trademark Office*